(12) United States Patent
Patil

(10) Patent No.: US 10,998,091 B2
(45) Date of Patent: May 4, 2021

(54) SYSTEMS FOR MONITORING COMPLIANCE WITH A PATCH DOSAGE REGIMEN AND METHODS OF USING THE SAME

(71) Applicant: Sandeep Patil, Menlo Park, CA (US)

(72) Inventor: Sandeep Patil, Menlo Park, CA (US)

(*) Notice: Subject to any disclaimer, the term of this patent is extended or adjusted under 35 U.S.C. 154(b) by 0 days.

(21) Appl. No.: 16/780,364

(22) Filed: Feb. 3, 2020

(65) Prior Publication Data

US 2020/0258610 A1 Aug. 13, 2020

Related U.S. Application Data

(60) Provisional application No. 62/853,885, filed on May 29, 2019, provisional application No. 62/809,451, filed on Feb. 22, 2019, provisional application No. 62/802,597, filed on Feb. 7, 2019.

(51) Int. Cl.
*G08B 23/00* (2006.01)
*G16H 20/10* (2018.01)
*A61B 5/00* (2006.01)
*A61P 25/28* (2006.01)
*G16H 40/67* (2018.01)
*A61K 9/70* (2006.01)

(52) U.S. Cl.
CPC .......... *G16H 20/10* (2018.01); *A61B 5/0022* (2013.01); *A61B 5/0028* (2013.01); *A61B 5/4088* (2013.01); *A61B 5/746* (2013.01); *A61K 9/7023* (2013.01); *A61P 25/28* (2018.01); *G16H 40/67* (2018.01)

(58) Field of Classification Search
CPC ......... G16H 20/10; G16H 40/67; A61P 25/28; A61B 5/0022; A61B 5/0028; A61B 5/4088; A61B 5/746; A61K 9/7023
USPC ...................................................... 340/573.1
See application file for complete search history.

(56) References Cited

U.S. PATENT DOCUMENTS 9,724,408 B2 8/2017 Dubensky, Jr. et al.
2004/0072733 A1 4/2004 Killam
2004/0229295 A1 11/2004 Marchitto et al.
(Continued)

FOREIGN PATENT DOCUMENTS

WO WO2009126653 A1 10/2009
WO WO2013142339 A1 9/2013

*Primary Examiner* — Naomi J Small
(74) *Attorney, Agent, or Firm* — Bret E. Field; Bozicevic, Field & Francis LLP

(57) ABSTRACT

Aspects of the invention include systems for monitoring compliance of a patient with a patch dosage regimen and, where necessary, providing rapid, economical intervention when non-compliance is detected. In some instances, the systems include: a patch comprising an active agent and a patch tag; a reader configured to detect the patch tag; one or more processing devices; and a compliance determination module comprising a computer-readable storage medium comprising instructions that, when executed by the one or more processing devices, determine compliance information from data received from the reader. The compliance information includes data that may be employed to determine whether the patient is complying with the patch dosage regimen. Also provided methods of using the systems, e.g., to monitor patient compliance, as well as components of the systems, e.g., patches, readers, etc.

19 Claims, 7 Drawing Sheets

(56) References Cited

U.S. PATENT DOCUMENTS

| | | | | |
|---|---|---|---|---|
| 2008/0008747 | A1* | 1/2008 | Royds | A61P 25/04 424/449 |
| 2008/0044461 | A1* | 2/2008 | Valia | A61K 9/7084 424/449 |
| 2008/0284599 | A1* | 11/2008 | Zdeblick | A61B 5/076 340/572.1 |
| 2009/0326516 | A1 | 12/2009 | Bangera et al. | |
| 2011/0071482 | A1* | 3/2011 | Selevan | G04F 3/08 604/307 |
| 2011/0150766 | A1* | 6/2011 | Royds | A61K 31/167 424/9.1 |
| 2013/0123719 | A1* | 5/2013 | Mao | A61M 35/00 604/304 |
| 2013/0184547 | A1* | 7/2013 | Taub | A61B 5/14532 600/365 |
| 2016/0331283 | A1* | 11/2016 | Rao | A61B 5/14503 |
| 2016/0371516 | A1* | 12/2016 | Debates | G06K 19/07345 |
| 2019/0110763 | A1* | 4/2019 | Brasch | A61B 5/0077 |
| 2020/0093375 | A1* | 3/2020 | Tseng | A61B 5/6832 |

* cited by examiner

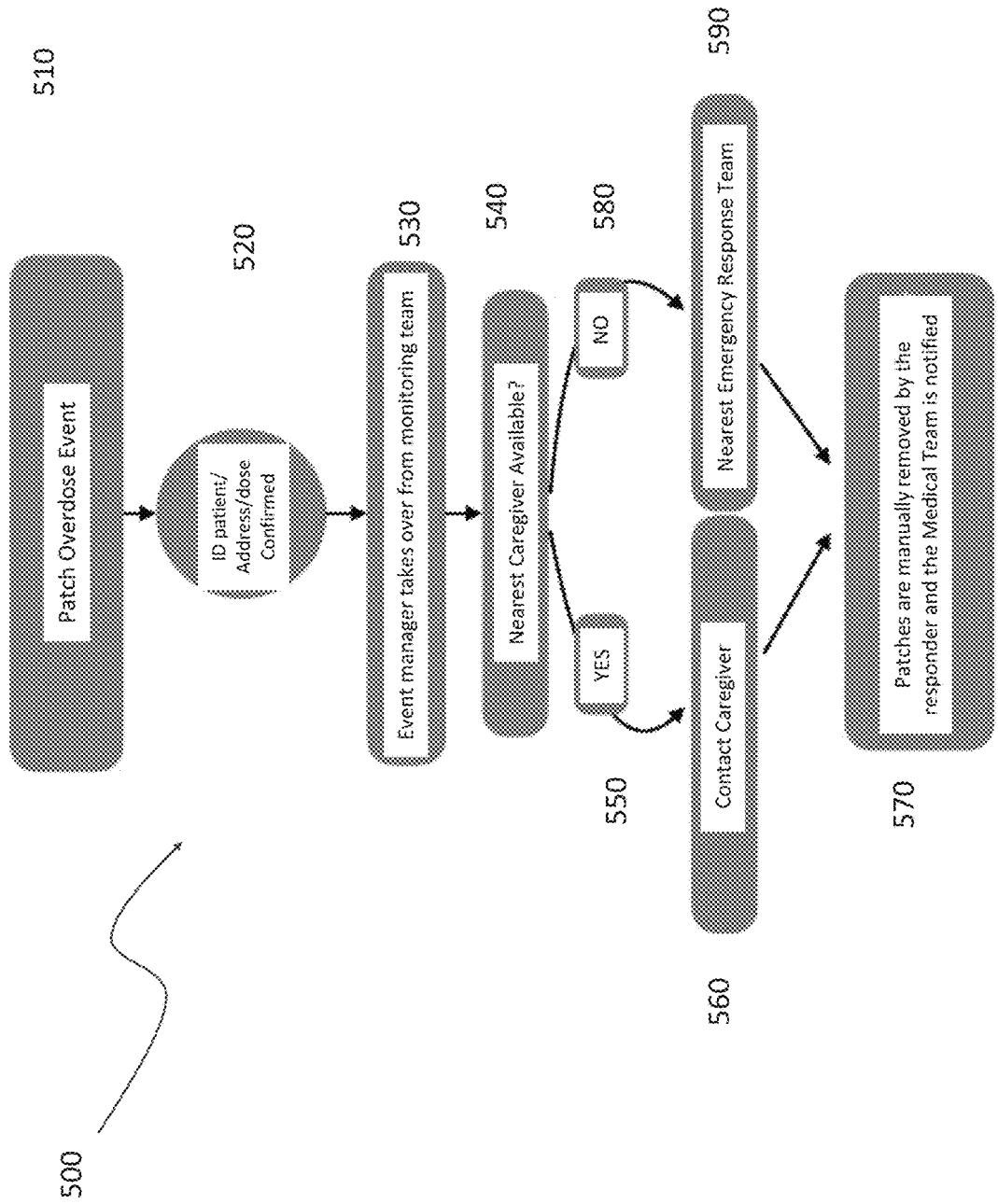

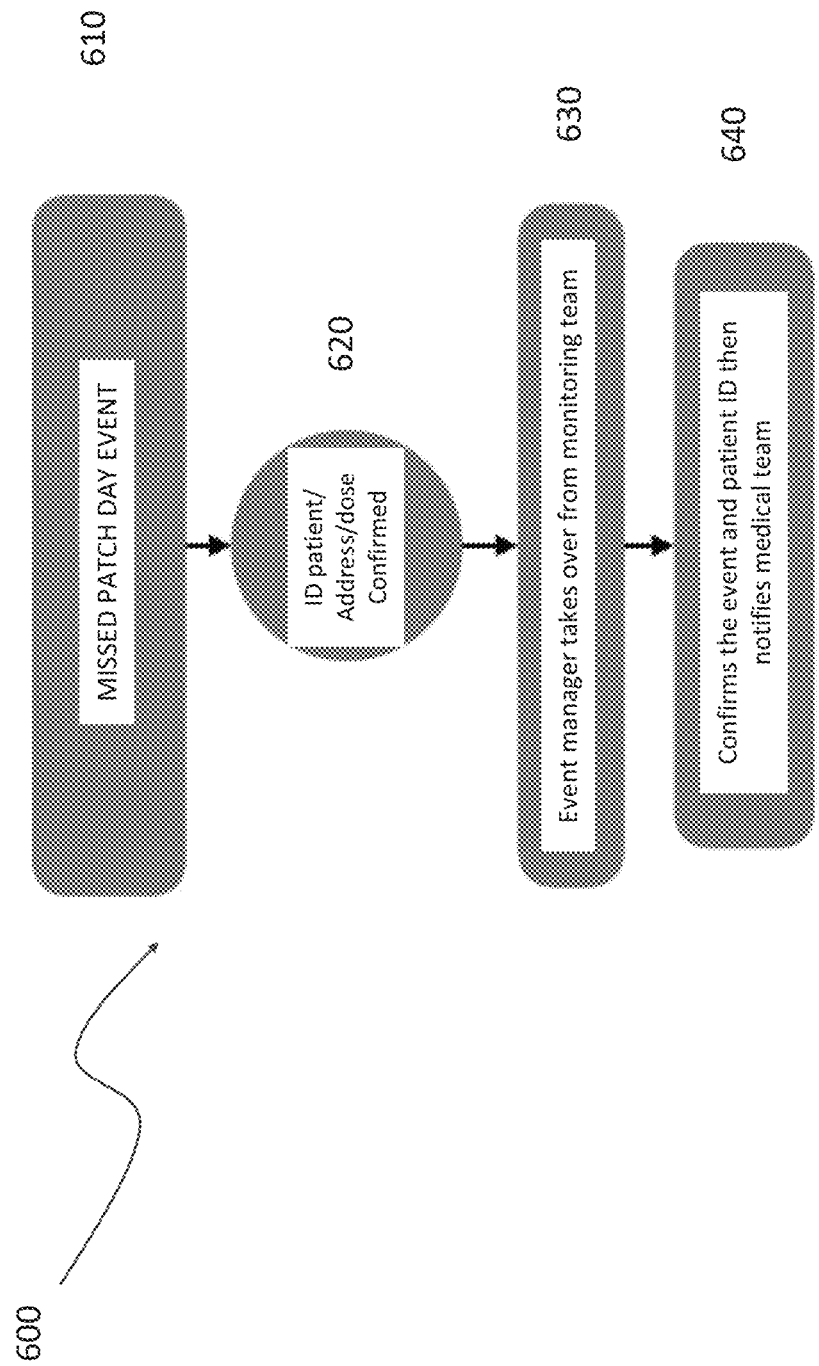

SYSTEMS FOR MONITORING COMPLIANCE WITH A PATCH DOSAGE REGIMEN AND METHODS OF USING THE SAME

CROSS-REFERENCE TO RELATED APPLICATIONS

Pursuant to 35 U.S.C. § 119(e), this application claims priority to the filing dates of: U.S. Provisional Patent Application Ser. No. 62/853,885 filed May 29, 2019; U.S. Provisional Patent Application Ser. No. 62/809,451 filed on Feb. 22, 2019; and U.S. Provisional Patent Application Ser. No. 62/802,597 filed Feb. 7, 2019; the disclosures of which applications are herein incorporated by reference.

INTRODUCTION

Millions of elderly patients suffering from Alzheimer's disease are prescribed memory loss drugs such as cholinesterase inhibitors, e.g., rivastigmine. Such drugs can be prescribed as an oral capsule/solution or by a transdermal delivery system (TDS) such as a skin or dermal patch (referred to herein as a "patch"), e.g., the Exelon® Patch (rivastigmine transdermal system). When administered orally, these drugs have uncomfortable gastro-intestinal side effects (e.g., stomach upset, nausea, vomiting, etc.) due to elevated levels of acetylcholine (Ach) neurotransmitter. Accordingly, a patch is the preferred option for the majority of the patients as it gives a steady dose of drug absorbed through the skin with reduced GI side-effects.

However, fatal outcomes or emergency hospitalizations have been reported due to "patch overdose" caused by inadvertently placing more than the prescribed number of patches on the body [1]-[3]. Such incidences of "patch poisoning/overdose" are not uncommon and manifest more seriously in the vulnerable patients suffering from memory impairment, physical fragility, and cognitive decline. This is facilitated by the fact that generally the total amount of drug in the patch is twice the amount of the drug that is delivered over the 24 hour dosing period [4], [5]. Serious physical harm is possible by mistakenly placing just two patches on the body at the same time. The symptoms from patch overdose can resemble common insecticide (carbamate) poisoning with symptoms due to elevated Ach such as, salivation, lacrimation, urination, defecation, GI cramps, emesis. In severe cases, this can lead to rapid dehydration and renal failure, as well as bradycardia potentially leading to sudden cardiac arrest and death. In 2018 alone, online Federal Adverse Event Reporting System (FAERS) Public database recorded more than 100 fatalities and several hundred more serious adverse events (SAEs) linked to the rivastigmine patch as the suspected product. The seriousness and frequency of the outcomes alarmed the United States Food and Drug Administration (FDA) and a warning to the prescribing information package was added (see Exelon Package Inserts [6]).

Elderly Alzheimer's patients living remotely at home with an elderly caregiver (who may be unfamiliar or underestimate the dangers of patch overdose) are at a higher risk, but overdose in hospitals and nursing homes has also been reported [2]. The manufacturer of the Exelon® Patch created a monthly tracking system in an effort to reduce the number of errors or mistakes in applying the rivastigmine patches. The system is called "Patch Tracker: A guide to when and where to place the patch". It consists of following instructions: Step 1: Write the date of application on the patch. Apply the EXELON PATCH (rivastigmine transdermal system) to your loved one in one of the possible application sites. Step 2: Record the same application date on the corresponding patch icon below. Step 3: After 24 hours, remove and discard the patch. Step 4: Repeat steps 1-3 with a new patch.

The Patch Tracker system is a guidance tool but is not specifically designed to protect the user if multiple patches are applied by mistake. A high rate of continuing SAEs and fatalities suggest that current approaches may not be as effective as hoped and there is a need for more user-friendly and effective solution(s).

SUMMARY

Inventor has realized that unlike oral route, a slower absorption of the drug through skin provides a safety window to prevent serious side-effects even if more than one patch is placed by mistake. However, there is no reliable way to quickly detect and stop patch overdoses (or non-compliance) before the condition becomes serious. Inventor has realized that what is needed is a system that places a minimal burden to participate on the patient or their caregiver, but is still effective in preventing serious outcomes due to patch non-compliance. Embodiments of the invention address this critical need.

Aspects of the invention include systems for monitoring compliance of a patient with a patch dosage regimen and where necessary, providing rapid, economical intervention when non-compliance is detected. In some instances, the systems include: a patch comprising an active agent and a patch tag; a reader (or a gateway node) configured to detect the patch tag and transmit the status to a monitoring center; and a compliance determination module comprising a computer-readable storage medium comprising instructions that, when executed by one or more processing devices, determines compliance information from data received from the reader. The compliance information includes data that may be employed to determine whether the patient is complying with the patch dosage regimen. Also provided methods of using the systems, e.g., to monitor patient compliance, as well as components of the systems, e.g., patches, readers, etc.

BRIEF DESCRIPTION OF THE FIGURES

The invention may be best understood from the following detailed description when read in conjunction with the accompanying drawings. Included in the drawings are the following figures:

FIG. 5 provides a flow chart 500 illustrating the process that is employed when a patch overdose risk is identified by the smart intervention system shown in FIG. 3.

FIG. 6 provides a flow chart 600 illustrating the process that is employed when a patch intolerance risk is identified by the smart intervention system shown in FIG. 3.

DETAILED DESCRIPTION

Figure 1:
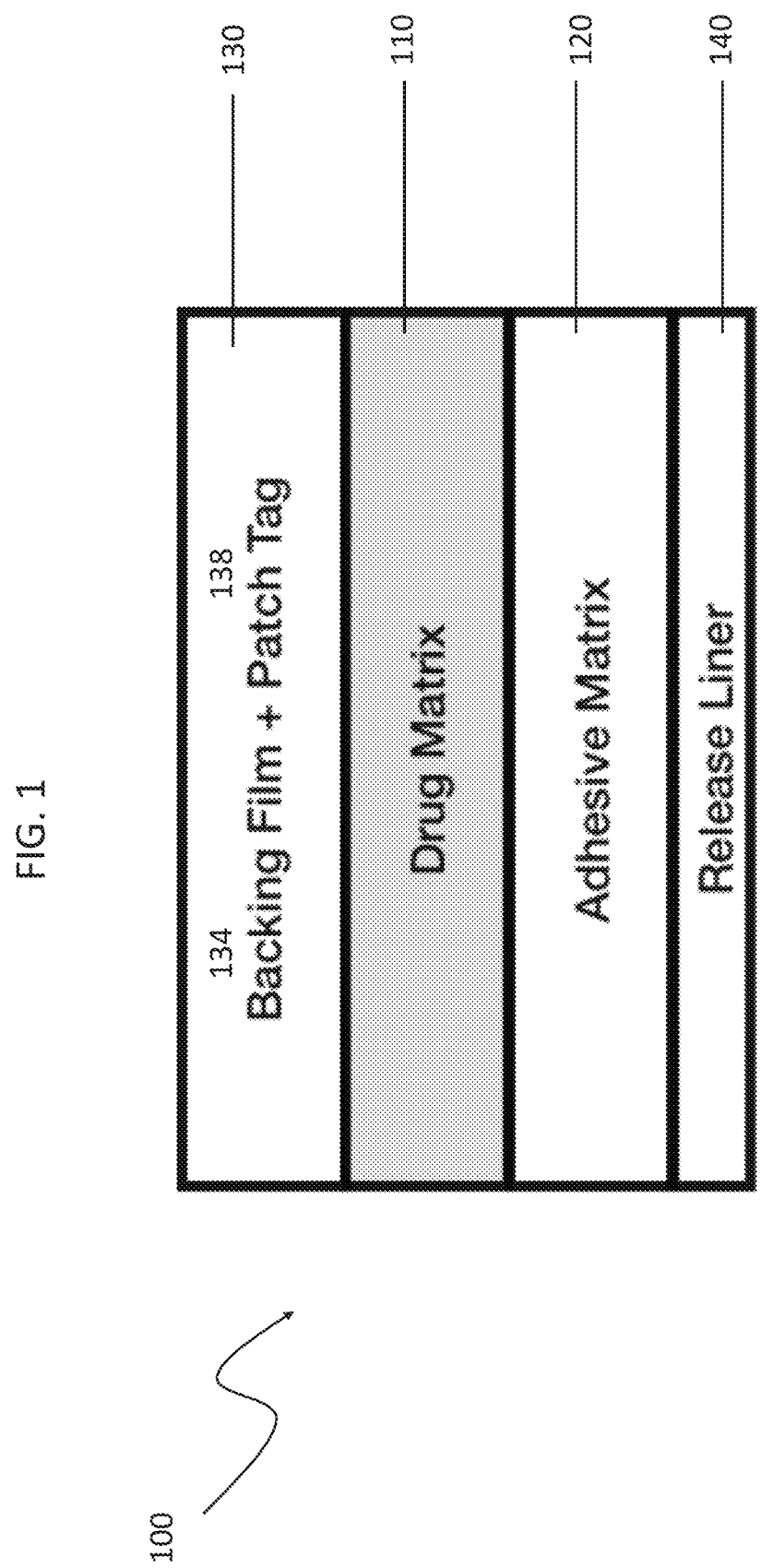
FIG. 1 provides a cross-sectional view of a rivastigmine topical patch that includes a patch tag in the backing layer, according to an embodiment of the invention.

Aspects of the invention include systems for monitoring compliance of a patient with a patch dosage regimen and, where necessary, providing rapid, economical intervention when non-compliance is detected. Embodiments of the present invention are based in part on the realization by the inventor that a slow initial absorption of a drug, e.g., rivastigmine, through the skin provides a safety window, e.g., of approximately 1-3 hours for rivastigmine, to create a system that may rapidly and economically prevent a patch mediated overdose. In some instances, the systems include: a patch comprising an active agent and a patch tag; a reader (e.g., gateway node) configured to detect the patch tag and, in some instances perform further processes, e.g., transmit data (such as to the internet); and a compliance determination module comprising a computer-readable storage medium comprising instructions that, when executed by the one or more processing devices, determines compliance information from data received from the reader. The compliance information transmitted by the reader includes data that may be employed to determine whether the patient is complying with the patch dosage regimen. Also provided methods of using the systems, e.g., to monitor patient compliance, as well as components of the systems, e.g., patches, readers, etc.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

Overview

As summarized above, the present disclosure provides systems and methods for monitoring patient compliance with a patch dosage regimen and, where necessary, providing rapid, economical intervention when non-compliance is detected. By "patch dosage regimen" is meant a schedule of doses of a therapeutic patch composition, including the time between doses. As such, a patch dosage regimen is the number of therapeutic patches that is applied to a patient at any given time, as well as the duration that each applied patch is maintained at the topical location of the patient. The number of patches that are applied to a topical location of a patient at any given time during a dosage regimen may vary, and in some instances ranges from 1 to 5, such as 1 to 3, where in some instances the number is one. The duration that a given patch is maintained at a topical location may also vary, ranging in some instances from 1 hour to 1 week, such as 6 hours to 4 days, including 12 hours to 3 days, e.g., 1 day or 2 days. In some instances, the patch dosage regimen is one patch applied per day, wherein a new patch is applied each day and any previously applied patch is removed.

Systems and methods as described herein may be employed to monitor patient compliance with a given patch dosage regimen. As such, the systems and methods may be used to determine whether a patient is or is not following a prescribed patch dosage regimen, such as whether a patient is following a prescribed patch dosage regimen or is deviating from a patch dosage regimen in some manner, e.g., by failing to apply a patch, e.g., where the number of applied patches is less than the number of prescribed patches, by failing to remove a patch and applying a second patch, e.g., where the number of applied patches exceeds the prescribed number of patches, etc.

Embodiments of systems described herein, which can be referred to as a Smart Intervention System (i.e., SIS), can dynamically track and identify a patient with a risk of therapeutic patch overdose and prevent a life-threatening situation, e.g., by initiating a predetermined sequence of events leading to a rapid and medically appropriate removal of all of the patches on the patient by direct human intervention. This sophisticated but still economical approach is especially designed for the patients who are cognitively impaired, e.g., due to an advancing neurodegenerative disease, such as Alzheimer's Disease, Parkinson's, or Lewy Body Dementia, Traumatic Brain Injury, and have put themselves unintentionally in danger of a patch overdose poisoning. As elements of removal of the patch in situations of overdose can be taught to nearby caregivers (prepopulated in Event Case Manager Database) even if they are not medical professionals (e.g., where such caregivers may be within approximately 30 min of distance from the patient) In the early stages the patient can be asymptomatic and in minimal danger (as significant amount of drug may not be yet absorbed transdermally), the SIS is designed to engage any EMS or medical team only as an alternative or a second option. In some instances, the system relies on more than one caregiver and actively seeks to pre-populate the database with such options. This approach is expected to increase the odds of finding a reliable caregiver in time (which is of essence), to reduce the cost significantly, and can increase caregiver's and patient's satisfaction thus avoiding automatic need for expensive emergency medical care. Furthermore, such a system may aid elderly patients who desire to live in the comfort of their own home longer than would otherwise be advisable or possible in spite of certain disabilities.

As described in greater detail below, systems of the invention can include a mix of purpose-built software systems, computerized database management, internet of things and electronic devices, therapeutic transdermal patches with built-in wireless communication technology, specialized therapeutic product dispensation, gateway device to cloud (internet), monitoring systems (human and electronic), specially trained event case managers, and medically appropriate human intervention to prevent a life-threatening injury. The higher level of complexity is due to a requirement of automatic and human-participated functions to provide a complete and highly time-sensitive patient care.

An important goal is to deliberately reduce the patient's, caregiver's and even medical team's burden to participate and not fundamentally change their preferred habit of using a transdermal patch. The medical team supporting the patient may be engaged on a (non-emergency) notification upon removal of the patch by the caregivers.

The systems may be designed to take into account the unique needs of the target population and still deliver the care in a cost-effective manner. Through the course of the neurodegenerative illness, patients progressively show deterioration of the usual self-awareness and self-preservation skills and are at a risk of unintentionally and gravely hurting their own health with the powerful medicines that are equally capable of causing severe harm, if used incorrectly, e.g., in deviance from a prescribed patch dosage regimen. An example of where deviance from a prescribed dosage regimen can occur is with cholinesterase patch dosage regimens in certain types of dementias. The mental status of patients prescribed such regimens may also fluctuate episodically. For example, such patients may be very lucid and get by easily for many weeks, and then may have sudden periods of confusion and poor function. To effectively deliver a cost-effective and patient-friendly care the monitoring system can have the adaptability and awareness about changing support needs during the emergency situation while not interfering at other times. For the system to function well, continuous visual monitoring of the patients in their place of residence is not necessary.

The need for SIS systems, e.g., as described herein, that resources cost effective solutions is growing as sky high health care costs reduce affordability of assisted or institutionalized care. The challenge is to monitor the target patient population unobtrusively and intervene when support is needed with urgency and purposefulness. Embodiments of the invention accomplish this goal by using technology in a unique way and incorporating patient-friendly human involvement in the most sensitive stage and where it is absolutely necessary to prevent physical harm. An SIS, e.g., as described herein, may be configured to continuously monitor the number of patches (enabled by signal from patch-tags, such as a tiny Bluetooth Low Energy "BLE" module, that can be incorporated at the time of manufacture) on a subject's body in their place of residence and will create "patch-events" in response to deviations from a prescribed dose regimen. In case of "patch overdose", the SIS may arrange for an expeditious human intervention to physically remove all the patches as soon as possible while in parallel notifying the medical team. The patch removal does not require a medical professional if the patient is approachable and cooperative with the caregiver. The nearest caregiver, spouse, or relative who is already registered (with consent) in a database that can be a part of the SIS. The system does not require the caregiver to be living with the patient. As a back-up, if no such person is available then assistance from local emergency services can be summoned. Caregivers can be educated to approach only if the patient is not in general distress, asymptomatic, and is cooperative (a likely situation with an early detection system). Emergency medical service (EMS) can also be summoned if the caregiver finds the patient to be uncooperative, medically ill, or aggressive. This approach is unique because, among other things, it allows for a flexible, low cost, rapid preventive action before a toxic amount of drug is received transdermally. Usually, removal of all patches as early as possible, for example, in 3 hours or less for the rivastigmine patch, may be all that is needed to keep the patient safe. New patch can then be applied per the medical team's recommendation or after a given period of time. Hospitalization and/or Emergency room visits can cost thousands of dollars and even worsen the patient's prognosis, for a generally preventable situation, such as a patch overdose.

Sudden high exposure of medication into the patient's body after many missed days can also lead to a medical emergency due to a phenomenon of "Patch Intolerance". In case of the "missed patch days", which can lead to patch intolerance, the SIS can mediate suitable intervention, such as alerting a caregiver to ensure that a patch (only one patch) is applied to the patient so that the patient is again in compliance with the patch dosage regimen, alerting a medical team of the missed patch day, etc. In case more than 2 patch days are missed there is an increasing danger of patch intolerance. Thus, in these situations the primary goal of the monitoring system is to notify the medical team which can then manage the patient's well-being as indicated in a non-emergency manner.

While systems of the invention may vary, in some instances the systems include the following components:

An informed consent that can be obtained from the patient and designated caregivers. The system preferably does not rely "only" on the primary (or regular) caregiver as timely intervention during an "event" alert is of high importance. Caregivers can be family members, relatives, spouse, partners, neighbors, volunteers, etc. It is possible that one of the above may be a regular (everyday) caregiver (such as a spouse), while others may be considered "ancillary" caregivers. Ancillary caregivers can serve as a back-up caregivers during "patch events" when the regular caregiver is unavailable or unreachable.

A therapeutic transdermal patch that can be specially manufactured with a signaling (patch) tag (and built-in ID) that will NOT interfere with the FDA-approved delivery of the drug. The whole composite patch can be manufactured in an FDA approvable manner.

A patch-tag that can be linked to the patient automatically when it is dispensed (for example, at pharmacy). The linked data can be sent to an SIS database and kept encrypted until an event.

A patch-tag that can connect to a monitoring system automatically (for example, via cloud-based systems) when patients apply it to their body. Other than this, the patient need not be expected to do anything more to participate in the benefits of the SIS system.

Capability such that when a patch-tag event (too many patches or missed patch days) is detected a smart intervention program can be initiated (see figures for the activity flow).

Systems and methods, e.g., as described herein, may be employed with a variety of different types of patches. Patches can be designed to continuously deliver a steady dose of various types of drugs, medicines, or other chemicals transdermally to a person, such as an elderly patient, an Alzheimer's patient, or any other person in need of treatment with a patch. For example, the drugs can be memory loss drugs, cholinesterase inhibitors, e.g., rivastigmine, or opiates, e.g., as reviewed below in greater detail. The solution can also be used with combinations of drugs from different patches that may enhance each other's toxicity if placed at the same time leading to emergency hospitalization, cholinergic poisoning, toxicity, or other undesirable effects including death.

If detected early and the patches removed in a reasonable amount of time the overdose can be stopped. Such a timely intervention to prevent patch overdoses can save lives and reduce costs (by preventing unnecessary hospitalizations, medical care due to overdose, emergency room visits, etc. which can rapidly escalate the health care costs). However, currently there is no reliable way to quickly detect and stop such patch overdoses before the condition becomes serious especially in memory impaired patients. The patient themselves may be completely unaware and the caregiver, even if nearby, may be either underinformed, unavailable, busy with chores, unaware of risks or frightened due to the worsening patient condition.

As described in greater detail below, in one embodiment, a patch to be applied to a person's skin can include a patch tag. The patch tag can include electronics configured to emit a signal indicative of the patch being attached to the patient's skin. The technology in the patch tag can signal the patch status to a gateway device or directly to a cloud (internet) connected device from anywhere in the house in a reliable and power efficient manner. In a further embodiment, a method for monitoring the use of patches on a patient is provided. Signals from one or more patches attached to a patient's skin can be continuously monitored (for example, once every second, minute, 5 minutes, or 30 minutes). When two or more signals from two or more patches attached to the patient's skin are received, an overdose alert can be triggered.

In reaction to an overdose alert the monitoring system can be configured to pass the information to a trained event manager who assumes the responsibility of confirming the overdose, patient ID, contacting a nearest caregiver (prepopulated in database) and if unavailable, contacting a nearest EMS. The caregiver or the emergency responder can then physically visit the patient, identify the patient, seek cooperation, and manually remove all the patches. If patient is in visible distress, medically unstable, or such an EMS will be promptly summoned by the caregiver. The event manager confirms the number of patches, their removal and then relays the information to the primary medical team. For patches such as rivastigmine patches, if the activity is performed in less than 3 hours it can be generally lifesaving. In certain situations, real world data, drug properties may be used to set the optimal threshold time. Missed patch dose (followed by suddenly applying a higher dose patch) is equally serious and, in those situations, the medical team is informed on second day (24-hour gap).

In a further embodiment, a patch detector can include a receiver and a processing system. The receiver can be configured to continuously monitor signals from one or more patches attached to a user's skin. The processing system can be coupled to the receiver and be configured to identify when two or more patches are applied to the skin of a single user at the same time. When that is detected, the processing system can trigger an alert locally.

Various aspects of embodiments of the invention are now described in greater detail.

Systems & Methods

As summarized above, systems and methods for monitoring compliance of a patient with a patch dosage regimen, e.g., as described above, are provided. Aspects of the systems include: a patch comprising an active agent and a patch tag; a reader configured to detect the patch tag; and a compliance determination module comprising a computer-readable storage medium comprising instructions that, when executed by one or more processing devices, determines compliance information from data received from the reader, wherein the compliance information includes data that may be employed to determine whether the patient is complying with the patch dosage regimen. Each of these system components is now reviewed in greater detail.

Topical Patch

The topical patch component of the invention is an active agent comprising composition that is configured to be applied to a topical location of a subject, e.g., patient. Topical patches are compositions that are configured to locally or transdermally deliver an active agent to a subject when topically applied to a skin surface of a subject. Topical patch compositions may include two or more layers, where the two or more layers may include at least an active agent containing layer and a backing.

Active Agent Layer

As reviewed above, topical patches described herein include an active agent layer. By "active agent" is meant a chemical compound that induces a desired pharmacological or physiological effect and include agents that are therapeutically effective or prophylactically effective. The term "active agent" also includes pharmaceutically acceptable derivatives and analogs of the active agent including, but not limited to, salts, esters, amides, prodrugs, active metabolites, analogs, polymorphs, solvates, hydrates, and the like. In some instances, the active agent layer includes one active agent (i.e., a single active agent). Active agent layers of interest include an amount of an active agent component present in a matrix, such as an adhesive matrix, such as described below.

The topical patch may include a variety of different active agents. Active agents that may be present in the layer include, but are not limited to: nonsteroidal anti-inflammatory analgesics (e.g., diclofenac, indomethacin, ketoprofen, felbinac, loxoprofen, ibuprofen, flurbiprofen, tiaprofen, acemetacin, sulindac, etodolac, tolmetin, piroxicam, meloxicam, ampiroxicam, naproxen, azapropazone, methyl salicylate, glycol salicylate, valdecoxib, celecoxib, and rofecoxib), antihypertensive agents (e.g., diltiazem, nicardipine, nilvadipine, metoprolol, bisoprolol, and trandolapril), anti-Parkinson agents (e.g., pergolide, bromocriptine, ropinirole, and selegiline), bronchodilators (e.g., tulobuterol, isoproterenol, and salbutamol), narcotic-based analgesic (e.g., fentanyl and morphine), urinary organ agents (e.g., oxybutynin), psychoneurotic agents (e.g., promazine and chlorpromazine), antidepressants (e.g., sertraline, fluoxetine, paroxetine, citalopram, and fluvoxamine), antidementia agents (e.g., donepezil, risperidone, rivastigmine, galantamine, and idebenone), expectorants (e.g., ambroxol), anti-anxiety agents (e.g., tandospirone), antipsychotic agents (e.g., olanzapine), analeptics (e.g., methylphenidate), osteoporosis treatment drugs (e.g., raloxifene and alendronate), breast cancer preventing drugs (e.g., tamoxifen), anti-obesity drugs (e.g., mazindol and sibutramine), anti-insomnia drugs (e.g., melatonin), steroids (e.g., estradiol, testoserone), nicotine, etc.

In some instances, the active agent is a cholinesterase inhibitor. Cholinesterase inhibitors or acetylcholinesterase inhibitors are medications that prevent the breakdown of acetylcholine in the body. Cholinesterase inhibitors block the action of acetylcholinesterase. Examples of cholinesterase inhibitors include but are not limited to donepezil, tacrine, rivastigmine, and galantamine. In some instances, the active agent is rivastigmine. Rivastigmine is an inhibitor of acetylcholinesterase and butyrylcholinesterase having the empirical formula $C_{14}H_{22}N_2O_2$. Rivastigmine is known chemically as (S)-3-[1-(dimethylamino)ethyl]phenyl N-ethyl-N-methylcarbamate and has the following formula:

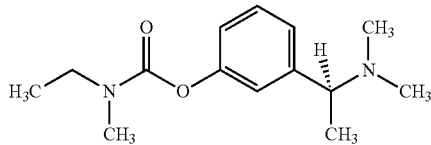 [SMILES: CCN(C)C(=O)Oc1cccc([C@H](C)N(C)C)c1]

The rivastigmine may be present in the active agent layer as a free base or salt. According to certain aspects, the rivastigmine is present as a salt. Rivastigmine salts of interest include, but are not limited to, rivastigmine tartrate, rivastigmine hydrochloride, etc.

The amount of active agent present in the active agent layer may vary. In some instances, the amount of active agent may range from 0.3 mg to 3 g, such as 0.8 mg to 2 g, including 1 mg to 1 g, e.g., 2 mg to 750 mg, including 3 mg to 500 mg. In some instances, the weight % of the active agent in the active agent layer (e.g., the adhesive matrix layer) ranges from 0.01% to 25%, such as 0.2% to 20%, including 0.3% to 15%. For example, the weight % of the active agent in the adhesive matrix may be 0.05% or more, such as 0.1% or more, including 0.5% or more, or 1% or more, or 2% or more, where in such instances the weight % may be 10% or less, e.g., 7.5% or less, including 5% or less. In certain embodiments, the weight % of the active agent ranges from 0.05 to 10% by weight of the adhesive matrix.

As summarized above, the active agent layer includes an amount of active agent in a matrix. In certain embodiments, the matrix is an adhesive matrix. The matrix may include polymeric materials. Suitable polymers for the adhesive matrix include, but are not limited to: polyurethanes, acrylates, styrenic block copolymers, silicones, and the like. For example, the adhesive matrix may include, but is not limited to, an acrylate polymer, polysiloxanes, polyisobutylene (PIB), polyisoprene, polybutadiene, styrenic block polymers, combinations of thereof, and the like.

Suitable styrenic block copolymer-based adhesives include, but are not limited to, styrene-isoprene-styrene block copolymer (SIS), styrene-butadiene-styrene copolymer (SBS), styrene-ethylenebutene-styrene copolymers (SEBS), and di-block analogs thereof.

Where desired (e.g., in configurations where the formulation is configured such that, during use, the active agent layer contacts the skin), the active agent layer (e.g., the adhesive matrix) may include a pressure sensitive adhesive. The terms "pressure sensitive adhesive", "self-adhesive", and "self-stick adhesive" mean an adhesive that forms an adhesive bond when pressure is applied to adhere the adhesive with a surface. In some instances, the adhesive is one in which no solvent, water, or heat is needed to activate the adhesive. In certain embodiments of pressure sensitive adhesives, the degree of bond strength is proportional to the amount of pressure that is used to apply the adhesive to the surface.

Pressure sensitive adhesives of the adhesive matrix include, but are not limited to, acrylate polymers. Acrylate polymers may include copolymers of various monomers which may be "soft" monomers or "hard" monomers or combinations thereof. Soft monomers are characterized by having a relatively lower glass transition temperature ($T_g$), and include examples such as, but not limited to, n-butyl acrylate, 2-ethylhexyl acrylate and isooctyl acrylate. Hard monomers are characterized by having a relatively higher $T_g$, and include examples, such as, but not limited to include styrene, methyl methacrylate, ethyl acrylate and methyl acrylate. The acrylate polymers can be composed of a copolymer including bipolymer (e.g., made with two monomers), a terpolymer (e.g., made with three monomers), or a tetrapolymer (e.g., made with four monomers), or copolymers made from greater numbers of monomers. The acrylate polymers can include cross-linked and non-cross-linked polymers. The polymers can be cross-linked by cross-linking agents to provide the desired cross-linked polymers.

Monomers from which the acrylate polymers are produced include at least two or more components selected from acrylic acids, alkyl acrylates, methacrylates, copolymerizable secondary monomers or monomers with functional groups, and the like. Monomers (e.g., "soft" and "hard" monomers) of interest include, but are not limited to, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, acrylonitrile, methoxyethyl acrylate, methoxyethyl methacrylate, and the like. Additional examples of acrylic adhesive monomers are described in Satas, "Acrylic Adhesives," Handbook of Pressure-Sensitive Adhesive Technology, 2nd ed., pp. 396-456 (D. Satas, ed.), Van Nostrand Reinhold, New York (1989), the disclosure of which is herein incorporated by reference. Acrylic adhesives, available from several commercial sources, are sold under the trade names AROSET, DUROTAK, EUDRAGIT, GELVA, and NEOCRYL.

The size (i.e., area) of the active agent layer may vary, but is within a range sufficient to provide for the desired delivery of a therapeutically effective amount of the active agent to the subject to which the patch is applied. In certain embodiments, the active agent layer is dimensioned such that it has an area that ranges from 2 cm$^2$ to 200 cm$^2$, such as 4 cm$^2$ to 150 cm$^2$, including 5 cm$^2$ to 100 cm$^2$, or 10 cm$^2$ to 80 cm$^2$, or 10 cm$^2$ to 60 cm$^2$. The active agent layer may vary in thickness. In some embodiments, the active agent layer has a thickness that ranges from 10 μm to 500 μm, such as 10 μm to 400 μm, including 10 μm to 300 μm, or 10 μm to 250 μm, or 10 μm to 200 μm, or 20 μm to 200 μm, or 20 μm to 150 μm, or 30 μm to 150 μm, or 40 μm to 150 μm, or 40 μm to 125 μm. In some embodiments, the active agent layer is substantially insoluble in water. By insoluble in water is meant that that the layer may be immersed in fixed volume of water (e.g., 500 times the weight of the active agent layer) for a period of 1 day or longer, such as 3 days or longer, including 1 week or longer, or 2 weeks or longer, or 1 month or longer, such as 1 day to 6 months, e.g., 1 week to 3 months, including 1 week to 1 month (such as 1 week), and exhibit no significant dissolution, e.g., substantially no observable dissolution, e.g., 0.2% or less dissolution, such as 0.1% or less dissolution.

Permeation Enhancer

In certain embodiments, the active agent layer includes a permeation enhancer. The permeation enhancer may facilitate the absorption of the active agent by the skin of the subject. The permeation enhancer may also be referred to as a percutaneous absorption enhancer.

The permeation enhancer may include, but is not limited to the following: aliphatic alcohols, such as but not limited to saturated or unsaturated higher alcohols having 12 to 22 carbon atoms, such as oleyl alcohol and lauryl alcohol; fatty acids, such as but not limited to linolic acid, oleic acid, linolenic acid, stearic acid, isostearic acid and palmitic acid; fatty acid esters, such as but not limited to isopropyl myristate, diisopropyl adipate, and isopropyl palmitate; alcohol amines, such as but not limited to triethanolamine, triethanolamine hydrochloride, and diisopropanolamine; polyhydric alcohol alkyl ethers, such as but not limited to alkyl ethers of polyhydric alcohols such as glycerol, ethylene glycol, propylene glycol, 1,3-butylene glycol, diglycerol, polyglycerol, diethylene glycol, polyethylene glycol, dipropylene glycol, polypropylene glycol, sorbitan, sorbitol, isosorbide, methyl glucoside, oligosaccharides, and reducing oligosaccharides, where the number of carbon atoms of the alkyl group moiety in the polyhydric alcohol alkyl ethers is preferably 6 to 20; polyoxyethylene alkyl ethers, such as but not limited to polyoxyethylene alkyl ethers in which the number of carbon atoms of the alkyl group moiety is 6 to 20, and the number of repeating units (e.g. —OCH$_2$CH$_2$—) of the polyoxyethylene chain is 1 to 9, such as but not limited to polyoxyethylene lauryl ether, polyoxyethylene cetyl ether, polyoxyethylene stearyl ether, and polyoxyethylene oleyl ether; glycerides (i.e., fatty acid esters of glycerol), such as but not limited to glycerol esters of fatty acids having 6 to 18 carbon atoms, where the glycerides may be monoglycerides (i.e., a glycerol molecule covalently bonded to one fatty acid chain through an ester linkage), diglycerides (i.e., a glycerol molecule covalently bonded to two fatty acid chains through ester linkages), triglycerides (i.e., a glycerol molecule covalently bonded to three fatty acid chains through ester linkages), or combinations thereof, where the fatty acid components forming the glycerides include, but are not limited to octanoic acid, decanoic acid, dodecanoic acid, tetradecanoic acid, hexadecanoic acid, octadecanoic acid (i.e., stearic acid) and oleic acid; middle-chain fatty acid esters of polyhydric alcohols; lactic acid alkyl esters; dibasic acid alkyl esters; acylated amino acids; pyrrolidone; pyrrolidone derivatives; and combinations thereof.

Additional types of permeation enhancers include, but are not limited to lactic acid, tartaric acid, 1,2,6-hexanetriol, benzyl alcohol, lanoline, potassium hydroxide (KOH), and tris(hydroxymethyl)aminomethane. Specific examples of permeation enhancers include, but are not limited to glycerol monooleate (GMO) and sorbitan monolaurate (SML), lactate esters such as lauryl lactate, methyl laurate, caproyl lactic acid, lauramide diethanolamine (LDEA), dimethyl lauramide, polyethylene glycol-4 lauryl ether (Laureth-4), lauryl pyroglutamate (LP), sorbitan monolaurate and ethanol, alone or in combinations of one or more. Of interest are permeation enhancers that are tailored to enhance permeation of surfactant type active agents. Examples of such permeation enhances include combinations of semi-polar solvents, e.g., propylene glycol, butane diol, N-methylpyrrolidone, dimethyl sulfoxide, diethylene glycol methyl ether, and dimethyl isosorbide, etc., and surfactants, such as isopropyl myristate, oleic acid, lauryl lactate, etc.

In some cases, the adhesive matrix contains the permeation enhancer in an amount ranging from 1% to 25% (w/w), such as from 1% to 20% (w/w), and including from 1% to 15% (w/w), or 1% to 10% (w/w). In certain cases, the adhesive matrix contains the permeation enhancer in an amount of 3% (w/w), or 5% (w/w), or 7% (w/w), or 9% (w/w).

Additional Components

In some embodiments, the polymer matrix includes a PVP. The term "PVP or "polyvinylpyrrolidone" refers to a polymer, either a homopolymer or copolymer, containing N-vinylpyrrolidone as the monomeric unit. PVP polymers may be homopolymeric PVPs and the copolymer vinyl acetate vinylpyrrolidone. The homopolymeric PVPs are known to the pharmaceutical industry under a variety of designations including Povidone, Polyvidone, Polyvidonum, Polyvidonum soluble, and Poly(1-vinyl-2-pyrrolidone). The copolymer vinyl acetate vinylpyrrolidone is known to the pharmaceutical industry as Copolyvidon, Copolyvidone, and Copolyvidonum. The term "soluble" when used with reference to PVP means that the polymer is soluble in water and generally is not substantially cross-linked, and has a molecular weight of less than about 2,000,000. The amount and type of soluble PVP used may vary. In some instances, the PVP is present in an amount from 1% to about 40% by weight, such as from 1% to about 20% by weight, based on the total weight of the polymer matrix. In some instances, the PVP has a molecular weight of 2,000 to 1,100,000 Daltons, including 5,000 to 100,000

Daltons, and 7,000 to 54,000 Daltons. The polymer may be crosslinked, such as for example crosslinked polyvinylpyrrolidone (PVP-CLM). Polyvinylpyrrolidone, such as PVP-CLM, PVP K17, PVP K30, PVP K90, that inhibit drug crystallization, have hygroscopic properties that improve the duration of wear, and improve the physical properties, e.g., cold flow, tack, cohesive strength, of the adhesive.

In certain embodiments, compositions may include a non-volatile solvent (i.e., a solvent that is non-volatile as compared to acetone, isopropanol or water, but may nonetheless exhibit some volatility), such as dimethyl sulfoxide (DMSO), N-methylpyrrolidone, dimethyl isosorbide, propylene glycol, hexylene glycol and benzyl alcohol. The non-volatile solvent may be present in a composition in an amount of between 1% and about 30%, such as 2 to 20% and including 3 to 15% by weight of the composition.

The topical patches may optionally include one or more antioxidants, such as but not limited to: tocopherol and derivatives, e.g., tocopherol acetate or tocopherol polyethylene glycol succinate, ascorbic acid and derivatives, e.g., ascorbyl palmitate, butylated hydroxyanisole, butylated hydroxytoluene, fumaric acid, malic acid, propyl gallate, metabisulfates and derivatives, etc. The antioxidant may be present in any convenient amount, ranging in some instances from 0.001 to 5.0% w/w of the formulation.

Where desired, the composition may further include one or more fillers. Fillers of interest include, but are not limited to: metal oxides (such as zinc oxide and titanium oxide), metal salts (such as calcium carbonate, magnesium carbonate and zinc stearate), silicic acid compounds (such as kaolin, talc, bentonite, Aerosil, hydrous silica, aluminum silicate, magnesium silicate and magnesium aluminometasilicate) and metal hydroxides (such as aluminum hydroxide). Where present, such fillers may be 1 to 75%, such as 2 to 50% by weight of the adhesive matrix component.

Multi-Layer Structure

As summarized above, the topical patches described herein may have a multi-layer structure. By multi-layer structure is meant that the patches include two or more distinct layers, where the total number of distinct layers in the patch composition may be two or more, such as 3 or more, including 4 or more, e.g., 5 or more. In some instances, the number of distinct layers may range from 2 to 5, such as from 2 to 4, including 2 or 3 layers. For example, the topical patch composition may have a matrix that includes the active agent, and a backing, where additional layers that may be present include adhesive layers, etc. The thicknesses of each of the layers in topical patch compositions may be the same or different, as desired.

Backing

As summarized above, the transdermal formulation may include a backing (e.g., support layer). The backing may be flexible to an extent that it can be brought into close contact with a desired topical location of a subject. The backing may be fabricated from a material that does not absorb the active agent and does not allow the active agent to be released from the backing side of the transdermal formulation. Backing materials of interest may be occlusive (i.e., impermeable), semi-occlusive or breathable (permeable). The backing may include, but is not limited to, non-woven fabrics, woven fabrics, films (including sheets), foils, porous bodies, foamed bodies, paper, composite materials obtained by laminating a film on a non-woven fabric or fabric, and combinations thereof.

Non-woven fabric may include, but is not limited to, the following: polyolefin resins such as polyethylene and polypropylene; polyester resins such as polyethylene terephthalate, polybutylene terephthalate and polyethylene naphthalate; rayon, polyamide, poly(ester ether), polyurethane, polyacrylic resins, polyvinyl alcohol, styrene-isoprene-styrene copolymers, and styrene-ethylene-propylene-styrene copolymers; and combinations thereof. Fabrics may include, but are not limited to: cotton, rayon, polyacrylic resins, polyester resins, polyvinyl alcohol, and combinations thereof. Films may include, but are not limited to the following: polyolefin resins such as polyethylene (including low density and high density polyethylene (LDPE, HDPE) and polypropylene; polyacrylic resins such as polymethyl methacrylate and polyethyl methacrylate; polyester resins such as polyethylene terephthalate, poly-chloro-tri-fluoro-ethylene, acrylonitrile methyl acrylate copolymer, polybutylene terephthalate and polyethylene naphthalate; and polyvinyl alcohol, ethylene-vinyl alcohol copolymers, polyvinyl chloride, polystyrene, polyurethane, polyacrylonitrile, fluororesins, styrene-isoprene-styrene copolymers, styrene-butadiene rubber, polybutadiene, ethylene-vinyl acetate copolymers, polyamide, and polysulfone; and combinations thereof. Foils of interest include metallic foils, e.g., aluminum foils, etc. Papers may include, but are not limited to, impregnated paper, coated paper, wood free paper, Kraft paper, Japanese paper, glassine paper, synthetic paper, and combinations thereof. Composite materials may include, but are not limited to, composite materials obtained by laminating the above-described film on the above-described non-woven fabric or fabric. In certain embodiments, the backing includes a polyester, such as polyethylene terephthalate (PET).

The size of the backing may vary, and in some instances the backing is sized to cover the desired topical target site. In some embodiments, the backing has a length ranging from 2 to 100 cm, such as 4 to 50 cm and a width ranging from 2 to 100 cm, such as 4 to 50 cm.

In some embodiments, the backing layer is insoluble in water. By insoluble in water is meant that that the backing layer may be immersed in water for a period of 1 day or longer, or 3 days or longer, or 5 days or longer, such as 1 week or longer, or 2 weeks or longer, including 1 month or longer, and exhibit little if any dissolution, e.g., no observable dissolution.

The backing layer may be in contact with a surface of the active agent layer. For example, where the formulation is configured so that one surface of the active agent layer contacts the skin upon application, the backing will be in contact with an opposing surface of the active agent layer.

Release Liner

In some embodiments, a release liner is provided on the active agent layer (i.e., the adhesive matrix), and specifically on a surface of the active agent layer that is distal (i.e., opposite) from the backing layer. The release liner may facilitate the protection of the active agent layer before use of the transdermal formulation. In certain cases, the release liner is configured to be removable from the adhesive matrix without retaining the adhesive matrix on the release liner.

The release liner may be any convenient material, where representative release liners include polyesters, such as polyethylene terephthalate, polypropylene, and the like. In certain embodiments, the release liner includes a coated substrate, which, for example, may be prepared by treating one side of polyethylene-coated wood free paper, polyolefin-coated glassine paper, a polyethylene terephthalate (polyester) film, a polypropylene film, or the like with a silicone treatment. In certain instances, the release liner includes a polyester film with a silicone treatment.

Adhesive Overlay

Optionally, an adhesive overlay can be used to increase the adhesion of the composition when applied to the skin. Adhesive overlays can include a layer of adhesive present on a backing material, such as a porous, non-porous, occlusive, or breathable backing material. The dimensions of the adhesive overlay are chosen to provide the desired functionality, where in some instances the dimensions are chose such that the adhesive overlay, when applied over the active agent formulation, extends some distance beyond one or more of the sides of the active agent formulation. In some instances, the area of the adhesive overlay exceeds the area of the active agent formulation by 5% or more, such as by 10% or more, including by 20% or more. During use, the adhesive overlay can be applied by the patients, by the care givers, or can be integrated in the kits.

FDA Approved Patch Compositions

In some instances, the topical patch is an FDA approved transdermal patch, such as: Butrans® Buprenorphine transdermal patch; Catapres-TTS® Clonidine transdermal patch; Estraderm® estradiol transdermal patch; Climara® estradiol transdermal patch; Vivelle® estradiol transdermal patch; Alora® estradiol transdermal patch; Vivelle-Dot® estradiol transdermal patch; Menostar® estradiol transdermal patch; Minivelle® estradiol transdermal patch; Combipatch® estradiol/norethidrone transdermal patch; Ortho Evra® Ethinyl oestradiol (EE)/Norelgestromin (NL) transdermal patch; Climara Pro® estradiol (E)/Levonorgestrel (L) transdermal patch; Duragesic® Fentanyl transdermal patch; Sancuso® Granisteron transdermal patch; Daytrana® Methylphenidate transdermal patch; Nitro-Dur® Nitroglycerin transdermal patch; Minitran® Nitroglycerin transdermal patch; Oxytrol® Oxybutin transdermal patch; Exelon® Rivastigmine transdermal patch; Neupro® Rotigotine transdermal patch; Transderm Scōp® Scopalamine transdermal patch; Emsam® Selegiline transdermal patch; Androderm® Testosterone transdermal patch; Nicoderm CQ® Nicotine transdermal patch; Nicorette® Nicotine transdermal patch; Habitrol® Nicotine transdermal patch; Zecuity® Sumatriptan transdermal patch; Qutenza® Capsaicin transdermal patch; Flector® Diclofenac epolamine transdermal patch; Lidoderm® Lidocaine transdermal patch; Synera® Lidocaine (L)/Tetracaine (T) transdermal patch; Salonpas® Menthol (M)/Methyl salicylate (MS) transdermal patch; Evamist® estradiol transdermal patch; and Axiron® testosterone transdermal patch. In some instances, the transdermal patch is an Exelon® rivastigmine transdermal patch, including EXELON® PATCH 4.6 mg/24 hours, AMCX, EXELON® PATCH 9.5 mg/24 hours, BHDI, and EXELON® PATCH 13.3 mg/24 hours, CNFU.

Patch Tag

As reviewed above, topical patches of systems of the invention also include a patch tag. A patch tag is any component that can be detected by a reader, e.g., as described in greater detail below, that is configured to detect a patch tag. The patch tag may communicate with the reader using any convenient protocol, including wireless communication protocols.

The patch tag may vary, so long as its association with the topical patch does not modulate, e.g., adversely impact, the functionality of the patch, e.g., to delivery active agent to the subject. As such, the patch tag can be configured to not modulate, e.g., interfere, with the drug delivery, dose, absorption qualities, adherence qualities, or other qualities of the patch that might change its effect on the patient wearing the patch. While the patch tag may vary, in some instances the patch tag has a small form factor, e.g., having a longest dimension ranging from 1 to 30 mm, such as to 2 to 20 mm, and included 5 to 15 mm. For example, the patch-can have a size of 2 cm×2 cm×2 cm or less. Examples of such patch tags include, but are not limited to: Bluetooth Low Energy ("BLE") tags, chip tags, RFID tags (including active or passive), beacon tags, etc. As the patch tag has a small form factor, it can be easily associated with, e.g., placed on, multiple styles of patches without significantly altering the thickness, weight, or size of the original patch with which it is associated. The patch tag may be present in any convenient portion of the patch composition, e.g., the adhesive matrix, the drug matrix, the backing layer, etc., where in some instances it is associated or part of the backing layer.

Where desired, the patch tag can consume either low power or no power (such as, passive HF or UHF RFID tags with a long-range Reader). Where the patch tag consumes power, it may be powered in a variety of different ways. The powering mechanism may be configured to draw power from body heat, a battery, movement of the person's body, electrical currents through the person's body, RFID interrogators, or other techniques, as desired. Examples of powering options that may be employed include, but are not limited to, battery free powering options, such as body heat harvesting elements, (e.g., the Renesas R7F0E controller), battery powering options, such as paper-thin batteries, vibration-based powering options, light-based powering options, or other minimal energy sources, etc. In some instances the power source is configured to provide power, upon activation, to the tag for 24 hours or longer, such as 48 hours or longer, e.g., 72 hours or longer, where in some instances the power source is configured to provide power for 96 hours or longer, such as 120 hours or longer, such as 144 hours or longer, and in some instances the power source is configured to provide power up to 168 hour or longer. In some instances, the power source is one that can be stored for extensive time periods prior to providing power to the activated patch tag, such as 6 months or longer, e.g., 1 year or longer, including 2 years or longer. Alternatively, the patch tag can optionally draw power from another device such as an interrogator in a passive RFID system or a battery-free Bluetooth chip. Where desired, the patch tag can include a sleep-wake system to allow the patch-tag to enter a sleep-mode to conserve energy (for example, while not attached to a user's skin).

Patch tags can also be designed to be activated at the time of administration, e.g., once they are placed on the skin or at another event near in time to placement on the skin, e.g., removal from packaging. For example, in some embodiments, the power source can be derived from a person's body, such that the patch tag only operates when applied to the person's body. In another embodiment, the patch tag can be packaged in a way such that it is activated upon opening the package or removing the patch-tag from the package. Electric-sensitive glue, or temperature sensor associated with the patch tag (e.g., chip thereof), or both in tandem with other technology can be used to activate the patch-tag when applied to the skin or removed from packaging. Similarly, a deactivating system can be set-up when the patch is discarded. Thus, a continuous signaling system is not required. Also, where desired the patch-tags can potentially provide additional body metric data by including relevant sensors attached to the patch.

Where desired, the patch tag can be activated such that it can signal a designated specially built detector also serving as a gateway or relay node to the cloud (referred to herein as a "gateway node") that will be placed within communication range with the patch-tag, when the skin patch is removed and placed on the skin, e.g., as described in greater detail below. The patch tag may be configured to provide wireless communication with such a detector over suitable distances, such as those found within a typically dwelling, where such distances may vary, ranging in some instances from 10 to 500 m, such as 100 to 250 m, where in some instances the distance is 1.5 m or longer, such as 5 m or longer, including 10 m or longer, e.g., 20 m or longer.

In some embodiments, a unique patch identifier is associated with the patch tag (for example, a unique number), such that each activated patch tag can be independently detected by its patch identifier. The unique identifier may also contain information on the authenticity of the patch, the dose and name of the therapeutic substance of the patch, as well as the useful shelf-life of the patch with which the patch tag is associated. In this way, any two patches on same person can be differentiated from a potential overdose signal due to a single medicine. In addition, any two patches on different people can be distinguished from each other. Furthermore, the patch-identifiers for the patch-tags can be registered in a database as being associated with a given patient/user who has received the corresponding patches (for example, from a pharmacist). For example, when a monthly prescription batch of patches is provided to a user, all of the patch-identifiers corresponding to the patches in that batch can be registered in the database as corresponding to that user. Alternatively, the patch-identifiers can be associated with a similar, anonymizing user-identifier, or a gateway node identifier corresponding to a node used by the patient. If patients have any digital identifiers (due to tendency to wander or possibility of being lost secondary to memory problems or advanced dementia) then such may also be employed as another way to associate a give patch-tag to a particular patient. Location based technologies can also be used and matched to the address of the patient already in the database, with the goal of minimizing the patient burden in signing in to any system for registering their tags.

Methods of Fabrication

Patches employed in systems/methods of the invention may be fabricated using any convenient protocol. In some embodiments, the methods include associating a patch tag with a patch configured to be applied to a dermal location, wherein the patch tag does not adversely affect active agent delivery from the patch. For example, the patch tag may be associated with the backing layer of a patch at the time of manufacture, such that it is integral with the patch following manufacture. The patch may be as described above, including a commercially available patch.

Specific Embodiment

FIG. 1 shows a cross sectional view of an embodiment of a patch that includes a patch tag. In FIG. 1, patch 100 includes four layers, drug matrix layer 110, adhesive matrix layer 120, backing layer 130 and release liner 140, which is removed at the time of use. Drug matrix layer 110 includes rivastigmine as an active agent. Backing layer 130 includes a backing film material 134 and a patch tag 138 associated therewith. The patch tag is associated with the backing film material at the time of patch manufacture and does not modulate rivastigmine delivery to the patient when the patch is topically applied to the patient.

Patch-Tag Reader

In addition to the tagged patches, e.g., as described above, systems of the invention further include a reader configured to detect a patch tag of a tagged patch. The reader is a device that can establish communication with a patch tag, such that it can receive information about the presence of a patch tag and the patch associated therewith on a patient. In some instances, the reader communicates wirelessly with the patch tag. "Communicating" information means transmitting the data representing that information as electrical signals over a suitable communication channel (for example, a private or public network). Any convenient telecommunications protocol may be employed for transmitting the data, e.g., facsimile, modem, internet, etc. In some instances, the reader is not a patient wearable device.

The reader may be part of a device remote from the location of the patient, e.g., where reader is capable of remotely detecting the patch tag, such as in those embodiments where the patch can directly and wirelessly communicate with a cellular network, the internet, etc. In such instances, the reader may be part of the same device that includes a compliance determination module or component(s) thereof of the system, e.g., as described in greater detail below. For example, a powered patch-tag can allow for direct signaling to remote devices without a patch-detector node, e.g., as describe below. For example, the patch tag can optionally include an antenna and associated components allowing for direct communication over WiFi or cellular networks, such that other devices can receive information related to the number of patches applied and emit an alert. This can optionally be allowed only if it is found to have the reliability and convenience of a Gateway Node, such as described below. By "remote location" is meant a location other than the location at which the patient is present, e.g., the patient's domicile, etc. For example, a remote location could be another location (e.g., office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart.

In some instances, the reader is part of a device that is distinct from the device comprising the compliance determination module, such as a reader device that is co-located with the patient. The terms "co-locate", "co-located" and "co-locating", as used herein refer to placing two or more devices in proximity (i.e., within a certain distance). In some aspects of the disclosed systems, co-located units may be located such that they are in the same building, e.g., patient domicile. In some aspects, co-located units may be located, for example, within 0.1 m; 1 m; 10 m; 100 m; of one another. In some instances of such embodiments, the reader is a component of a gateway. The term "gateway" is used in its conventional sense to refer to a piece of networking hardware used in telecommunications for telecommunications networks that allows data to flow from one discrete network to another. Gateways are distinct from routers or switches in that they communicate using more than one protocol and can operate at any of the seven layers of the open systems interconnection model (OSI).

For example, a gateway node may be employed where limitations exist in terms of direct cellular or other seamless connection to the internet, e.g., cloud, either due to power needs or size from the patch tag, e.g., where the patch tag is a tiny BLE node. In such instances, the gateway node can be engineered to receive a signal from the patch tag from anywhere that the patient might be at a given time, such as from anywhere in the patient's entire house. A number of advantages may be obtained in systems where a gateway node is employed. For example, the system may provide certain essential functions which can be exceptionally customized leading to superior overall product. At a base level a proprietary gateway node (such as a BLE receiver node plugged into electric socket and capable of transferring data to cloud from cellular or WiFi or by other mode as needed) can receive periodic signals from a patch tag when the node and patch are activated and will forward them by cellular or other mechanism to the monitoring center, e.g., where the compliance determination module is present. The gateway node can similarly request that the patch tag provide these signals when desired, thus allowing the patch-tag to preserve power when the signals are not necessary. The gateway node can then transmit data to a monitoring center connected by wire or wirelessly (for example, a processor on a nearby computer, or through a cloud-provided service, by a WiFi network, cellular network, or other networks), periodically or continuously with a built-in algorithm to detect if more than a certain threshold number of separate patches are applied to the person. Alternatively, the node and processor can be configured to identify a quantity of activated patch-tags by a strength or quantity of signals received. For example, if a single patch-tag emits a single signal at a known strength, then detection of two signals or a signal of double the known strength would indicate that two patch-tags are activated instead of only one. In some instances, only one patch is prescribed so a second patch will be enough to indicate a potential overdose and trigger a corresponding notification. Similarly, the node can optionally trigger a notification when a patient who is supposed to wear a patch appears to not be using a patch for an extended period of time (for example, having missed 2 days of patches).

The reader can be self-powered, e.g., by battery, or plugged-in to an outlet. The reader can be one in which no daily or frequent charging is indicated and the reader itself can be monitored by the system and predetermined trained caregivers can be alerted if the reader malfunctions or loses power. A replacement reader may be provided as necessary. The reader can also serve as a geo-location tool. The reader may also be configured to summon closest predetermined trained caregivers during time of need, e.g., as described below.

Where desired, a local alarm (such as a visual or auditory alarm) can be included as a part of the gateway node or near the node, and this alarm can be triggered if the number of detected activated patches are different from the prescribed number (for example, greater than one), as discussed above. Such application though may be particularly appropriate in a nursing home or in an Assisted Care facility as a medically trained professional will be already in the vicinity and may use the alarm to recheck and react to any error instantly. In other instances, such a local alarm may not be desired. For example, such a local alarm in a remote home may cause additional confusion or agitation, especially if the patient is alone or in presence of an untrained companion. In this case, the SIS offers a more reliable and compassionate care to prevent overdose via a trained human who can reassure the patient and assess the need for additional medical intervention. Similarly, an alarm can be provided through a processor wirelessly communicating with the node through various networks as described above. The patch-tag and the gateway node can detect a number of patches applied and create an alarm when too many patches are applied simultaneously, without significant effort from the patch users, caretakers, hospital staff, or other responsible people.

The proprietary gateway node can be a plug-in device or a battery-powered device or both. For a given system, the gateway node can be dispensed for free at the time of first prescription (such as at Pharmacy) or provided by mail etc. Such gateway nodes can be inexpensive and can be easily replaced every few months or yearly or when needed. Their functioning can be checked remotely and patient or his companion can be called by phone to provide instructions or replacement if malfunction is detected.

When present, the gateway node can be generally open to provide its services to any of the patch tag IDs in its range (e.g., and not tied to a single patient). Where desired, it can be limited to identify, and report only "authenticated" patch tags that are cleared by the designated manufacturers, identified in database as currently in circulation, and have not reached the predefined expiry date (coinciding generally with the patch expiry date). The patient or caregiver do not need to enter password to transmit the message through the node. The node and patch tag can auto-engage with each other. Filtering out expired patches and their patch IDs can also be conducted optionally at SIS database levels before any review by the human monitors. Thus, a filtering mechanism may be provided at the gateway node level (to reduce signal clutter) and also at the central SIS database level before the data is seen by a human eye.

The range of the gateway may vary, where in some instances the gateway has a range from (which can be modified electronically will usually cover at a minimum 10 to 500 $m^2$, such as 100 to 250 $m^2$, e.g., 185 $m^2$ (approximately 2000 $ft^2$). As such, the node can optionally have a range to cover a room, whole house, or whole building or even wider area for catching signals from one or multiple patch-tags. The range of the patch-detector node can be chosen to prevent detection of patches on more than one person, such as in a hospital setting where multiple patients could be using a patch. In some embodiments, the range of the node can be adjustable. Alternatively, the gateway node can be configured to monitor the number of patches on multiple patients, distinguishing the patches applied to each patient.

The connection/pairing to authenticated patch-tags may be automatic such that no sign-on or other requirements are necessary. For security reasons, the gateway node may not connect to any unauthorized blue-tooth device. The central database may store the IDs of all the authenticated patch tags in circulation while keeping it updated daily or hourly as determined by the usual circulation pattern of the patch tags. A dedicated phone app may be considered in certain situations but at this time it is not considered to be as reliable or convenient for the targeted population. However, it can be made available to the patients and caregivers as a convenience but not as a replacement for the gateway node.

In one embodiment, a single BLE receiver (or other Gateway node) and multiple patch-tags can be configured such that the node can monitor patch signals from multiple patients or subjects in a close vicinity (for example, patients 2 meters or further away, e.g., 10 meters or further away, such as 50 meters or further away, including within 500 meters, within an area of 185 $m^2$ (approximately 2000 sq.ft.), or on multiple floors in a single building). Different patches can be identified as being applied to particular people in a variety of ways. For example, each patch-tag can include a unique patch-identifier, and a set of those patch-identifiers can be known to correspond to a single person. Thus, false alarms can be prevented if two subjects wearing patches are sitting close to each other.

Power sources, e.g., batteries, included with the patch tag can optionally last for 24 hours or longer, e.g., as reviewed above. More generally, a battery can be configured to last at least as long as the patch is intended to be applied to a patient before being replaced or otherwise removed. When the patch will not have enough drug remaining after a certain period of time, the battery can be configured to last for at least that period of time. When the patch tag's battery lasts longer than the drug of the patch, and an additional patch on the person is detected, an alert can still be triggered but this alert can optionally indicate that an overdose is less likely or can otherwise have a reduced urgency. The gateway node can also power a battery-free patch-tag when applied by the patient.

There may also be a system in place such that when one patch is removed it turns off its patch tag automatically (for example, with electric conducting glue technology or a temperature sensor on the chip). In this way multiple signals from discarded patches may be avoided if the battery lasts more than 24 hours and is capable of sending signal when disposed away from the body. As discussed above, the patch-tag can optionally also draw power from a user's body, such that it will lose power upon removal. Further, the patch-tag can optionally be bent, crushed, or otherwise broken when removed from the skin.

Compliance Determination Module

As summarized above, systems of the invention further include a compliance determination module. The compliance determination module includes a computer-readable storage medium comprising instructions that, when executed by one or more processing devices, determines compliance information from data received from the reader, e.g., as described above, and, where necessary, provide rapid, economical intervention when non-compliance is detected, wherein the compliance information includes data that may be employed to determine whether the patient is complying with the patch dosage regimen. The compliance determination module is made up of one or more functional blocks which act in concert to perform a particular function, i.e., to determine compliance information from data received from the reader. A given compliance determination module may be implemented as hardware, software or a combination thereof. In some instances, modules may include a circuitry element, such as an integrated circuit. When present, integrated circuits may include a number of distinct functional blocks, where the functional blocks are all present in a single integrated circuit on an intraluminal-sized support. By single integrated circuit is meant a single circuit structure that includes all of the different functional blocks. As such, the integrated circuit is a monolithic integrated circuit (also known as IC, microcircuit, microchip, silicon chip, computer chip or chip) that is a miniaturized electronic circuit (which may include semiconductor devices, as well as passive components) that has been manufactured in the surface of a thin substrate of semiconductor material. In some embodiments, integrated circuit devices of interest include a field programmable gate array (FPGA). In other embodiments, integrated circuit devices include an application specific integrated circuit (ASIC). In yet other embodiments, integrated circuit devices include a complex programmable logic device (CPLD).

As stated above, the compliance determination module is configured to determine compliance information from data received from the reader and, where necessary, provide rapid, economical intervention when non-compliance is detected. The compliance information may vary. As such, the compliance information may be a simple assessment that the patient is or is not in compliance. In other instances, the compliance information may include more detailed data about the number of patches a patient is wearing at a given time. For example, the compliance information may include a determination of the number of patches applied to a patient, e.g., whether a patient has 0, 1, 2, 3 or more patched applied to her/him. Furthermore, the compliance determination module may be configured to determine whether or not a patient is in compliance with their prescribed patch dosage regimen, where this determination is made from the compliance information, which in turn is based on data received by the module from the reader of the system, e.g., a gateway node or directly from a patch tag, e.g., as described above. Accordingly, the compliance determination module can be configured to determine whether a patient is deviating from the patient's prescribed patch dosage regimen, e.g., by having too many or too few applied patches. For example, a patient may be determined to be in non-compliance with the patch dosage regimen if a determination of a number of patches applied to a patient deviates from the patch dosage regimen. For example, where the patch dosage regimen is a single patch at a time, e.g., 1 patch every 24 hours, the compliance determination module may determine the patient to be in non-compliance with the patch dosage regimen if the compliance information is that the patient is wearing 2 or more patches or no patches.

In some instances, the compliance determination module is further configured to output the compliance information to an event manager. An event manager is an individual that is trained to receive the compliance information and take appropriate action based thereon, e.g., alert a predetermined trained caregiver, healthcare professional, etc., that intervening action is required, e.g., to prevent an overdose or intolerance.

For example, when one or more patches are distributed to a patient their patch-identifiers can be registered in a database as corresponding to that patient. A pharmacist distributing the patches in response to a prescription can submit the information to a monitoring center (for example, using the internet or another communications protocol), which center can use this information to generate a database with information regarding patch identifiers and their corresponding patients. Again, an anonymizing patient identifier can be used, instead of or along with the patient's name. The database can additionally include a list of predetermined trained caregivers (such as 1 to 10 individuals that are predetermined, i.e., they have been identified, trained, obtained informed consent from the patient to intervene, etc.) and medical professionals or Emergency Medical Services (EMS) authorized to take action in the event of a detected misuse of the patches (e.g., along with contact information for them (for example, a phone number or email address)). The monitoring center can also include a compliance determination module.

A gateway node located near the patient (such as in a patient's home, in a hospital, or in an assisted-living facility), can monitor patch-tags applied to one or more patients within its range. The gateway node can then report the patch-identifiers that are activated and applied to a patient's skin to the monitoring center. The compliance determination module of the monitoring center can then determine from the received data if the patches for one or more patients are being used correctly and if there is a potential overdose or underuse (which could lead to a developed intolerance). In the event of such a risk, the information will be output to an event manager. Where the event manager is physically co-located with the compliance determination module, e.g., where the event manager is an employee of the monitoring center that houses the compliance determination module, the compliance determination module may output the information directly to the event manager. Alternatively, where the event manager is remote from the compliance determination module, the compliance determination may contact the event manager and provide the information, e.g., directly or via another individual, such as where an employee of the monitoring center contacts an event manager (by phone, text or email).

A trained event manager, e.g., as described above, then follows through a predetermined sequence of activities to accomplish the goal of returning the patient to compliance with their prescribed patch dosage regimen, e.g., via removal of the overdose patches from the patient's body or application of one or more patches to the patient's body. After verifying the details from the monitoring center, the event manager may first call the qualified caregivers, e.g., as described above. For the patients living at home the pre-qualified caregivers can be family members, spouse, partner, neighbors, or nearby friends who have consented to be available to visit the patient during an overdose emergency when contacted by the event manager. Involvement of the prescreened caregivers offers unique advantages in this method. It is expected to increase the patient and the caregiver satisfaction, ensure quick access during the emergency, reassure patient during their time of need, allow for a speedy resolution of the problem, provide a safer intervention, and reduce the health care costs greatly. The caregiver information and database may be reviewed periodically and at least once a year by a regional event manager. In some embodiments a minimum of 2 and maximum of 5 qualified caregivers per patient can optionally be added to the database and geographical proximity and access to the patient during the emergency may be a key criterion. Predetermined caregivers may be educated on basic procedural guidelines at the time of the informed consent and may be able to communicate with the event manager on an ongoing basis during the emergency. Before removal of the patches they may be instructed to slowly approach the patient and explain in simple, pleasant terms the purpose of their sudden visit. Once they have the confidence and cooperation of the patient they may be trained to inspect, count, remove and record the patches, and submit this information to the event manager within a reasonable period (for example, 24 hours). If the patient is uncooperative, they may be instructed to contact a health care provider, such as an EMS, for further care. A signed written agreement on such procedures can be required before they can qualify as a caregiver for an overdose emergency. A maximum time limit can be imposed (for example: 30 minutes) between their acceptance of the request and delivery of the care during the time of emergency. The event manager can be free to call emergency services such as EMS if the overdose patches are still detected on the patient after the wait period. Generally, EMS is expected to be called once the caregivers are found to be unavailable however, in certain situations (for example, if multiple patches are detected), the event manager can contact EMS directly before contacting any of the caregivers. The attendant or nurse can serve the function as a first responder if the overdose emergency is noted in the nursing home or assisted care facility.

Figure 2:
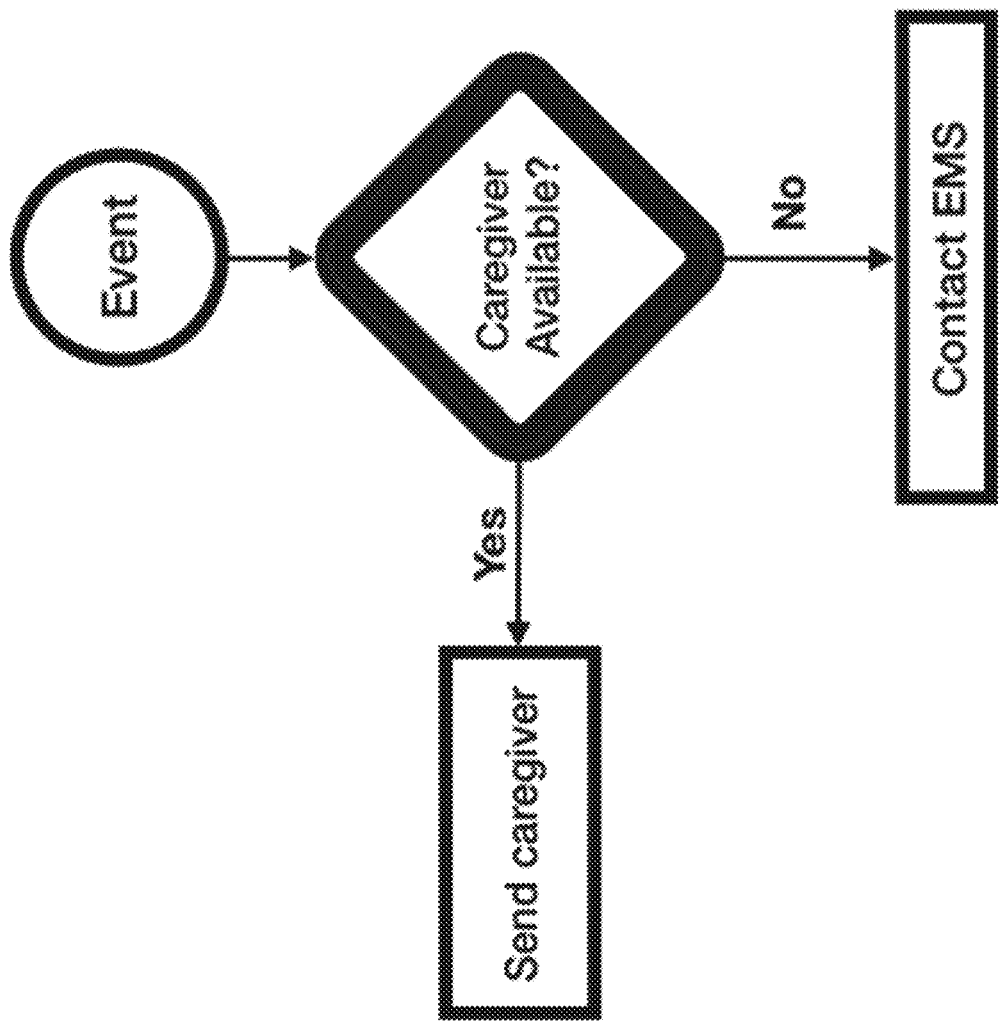
FIG. 2 provides a flow chart of an event manager mediated process in accordance with an embodiment of the invention.

An example of the above described event manager mediated process is illustrated in FIG. 2. In FIG. 2, a system according to an embodiment of the invention is employed, where the system comprises a database that is specifically designed for an effective intervention in a rapid manner while maintaining the patient well-being, caregiver satisfaction, and reduction in the costs by preemptively removing the patches before emergency care is needed. As illustrated in the flow chart of FIG. 2, the event manager receives information regarding a patch event. The event manager then determines if a predetermined trained caregiver is available to provide the appropriate intervention, e.g., remove patches applied to the patient. If a predetermined trained caregiver is available, the event manager sends the predetermined trained caregiver to the patient to provide the desired intervention. Specialized services such as Emergency Medical Services (EMS) or Ambulances are summoned by the event manager if the patient is symptomatic or a predetermined trained caregiver cannot reach the patient in a given amount of time. These outcomes are achieved in a structured manner as follows:

1. The database of the system contains contact information (among other types of information) for 1 to 10, such as 3 to 8, e.g., 5, nearby predetermined trained caregivers. As proximity to the patient is important for these predetermined trained caregivers to reach the patient in a timely manner, e.g., within 3 hours, such as within 2 hours, the predetermined trained caregivers may be individuals that at spend time within a reliable three hour or shorter travel distance to the patient, e.g., they work and/or reside within the same location, e.g., county or portion thereof, such as municipality, e.g., city or town, or subdivision thereof.
2. As such, the predetermined trained caregivers do not have to be living with the patient in the same house but can reach the patient in less than 2 hours during a patch event (such as within 30 min of a patch event).
3. Predetermined trained caregivers may be volunteers. As described above, they need not be health care professionals or medical personnel. Furthermore, they may not be compensated for time or travel costs.
4. Predetermined trained caregivers may be individuals that agree to a written consent and agree to follow the "patch removal process" in accordance with provided training. The training can specifically include appropriate ways to approach a patient with dementia.
5. The training given to the predetermined trained caregiver can include proper way to approach, inspect, confirm and remove the patches.
6. The database can be updated quarterly, monthly, yearly, as necessary, and in some instances is updated on at least a yearly basis (where for certain high frequency patients the update process can be customized consent can be updated every 1-5 years).
7. The system can be designed in a flexible manner, for example, if the patient is symptomatic and in obvious distress, then the predetermined caregivers may be instructed to immediately notify the event manager who will then arrange Emergency Medical Services (EMS). In some instances, the predetermined trained caregiver can also call EMS directly, where in such instances the predetermined trained caregiver may still inform the event manager, e.g., by text, email or phone call etc. as soon as possible.
8. The sequence by which predetermined trained caregivers are contacted by the event manager may be based on the geographical proximity to the patient and also by the caregivers, patient's and/or their guardian preference. An event manager may have final discretion on managing the patch removal.
9. The database may include the local EMS contact information, medical team contact information, etc. The database may or may not include additional information, such as the full patient medical history, concurrent medications, etc.
10. Predetermined trained caregivers may be spouses, relatives, neighbors, local volunteers, etc. If the predetermined trained caregiver is not known to the patient or their guardians, then a background check can be conducted prior to adding their names to the database of the system. The predetermined trained caregiver could also be a locally available alternative resource such as an Uber Health driver or such service, and can be summoned at the discretion of the event manager. As such resources are already prescreened by their employers additional screening may not necessary. However, prior patient consent may be required to use such local resources.

11. If no caregiver is available within a predetermined set time, e.g., 30-60 min following determination by the event manager that intervention is necessary, the event manager can contact EMS as a back-up.

Where desired, similar monitoring actions can also be performed by the gateway node, independent of a separate monitoring center. For example, the gateway node can optionally include a compliance determination module, e.g., as previously described, such that the gateway node can determine a potential overdose or underuse and provide the corresponding alerts, e.g., to an event manager, such as described above. Instead of a pharmacist providing information to assign the patch-identifiers to a patient, this can be performed by the patient or a caregiver using an input device in wired or wireless communication with the gateway node.

Computer Implemented Embodiments

The various algorithm steps described in connection with the embodiments disclosed herein can be implemented as electronic hardware, computer software, or combinations of both. To clearly illustrate this interchangeability of hardware and software, various illustrative steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative steps, components, and computing systems (such as devices, databases, interfaces, and engines) described in connection with the embodiments disclosed herein can be implemented or performed by a machine, such as a general purpose processor, a graphics processor unit, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor can also include primarily analog components. A computing environment can include any type of computer system, including, but not limited to, a computer system based on a microprocessor, a graphics processor unit, a mainframe computer, a digital signal processor, a portable computing device, a personal organizer, a device controller, and a computational engine within an appliance, to name a few.

The steps of a method, process, or algorithm, and database used in said steps, described in connection with the embodiments disclosed herein can be embodied directly in hardware, in a software module executed by a processor, or in a combination of the two. A software module, engine, and associated databases can reside in memory resources such as in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An exemplary storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Utility

Systems and methods of the invention, e.g., as described above, find use in monitoring a patient for compliance with a prescribed patch dosage regimen and, where necessary, providing rapid, economical intervention when non-compliance is detected. A variety of different patch dosage regimens for treatment of a variety of different conditions may be monitored with systems and methods as described herein. Examples of patch dosage regimens and there disease indications that may be monitored by systems and methods of the invention include, but are not limited to: treatment of female hormone replacement therapy with an estradiol transdermal patch dosage regimen; chronic pain with a buprenorphine patch dosage regimen; hypertension with a clonidine patch dosage regimen; chronic pain with a fentanyl patch dosage regimen; ADHD with a methylphenidate patch dosage regimen; angina pectoris with a nitroglycerin patch dosage regimen; overactive bladder with a oxybutynin patch dosage regimen; cognitive condition such as Alzheimer's and Parkinson's disease with a rivastigmine patch dosage regimen; Parkinson's disease with a rotigotine patch dosage regimen; major depressive disorder with a selegiline patch dosage regimen; hypogonadism with a testosterone patch dosage regimen; etc.

In some instances, the patient suffers from a cognitive disorder, such as Alzheimer's Disease, Parkinson's Disease, or Lewy Body Dementia. In such embodiments, the patient may be prescribed a cholinesterase inhibitor, e.g., rivastigmine, patch dosage regimen and the methods and systems are configured to monitor compliance of the patient with the prescribed a cholinesterase inhibitor, e.g., rivastigmine, patch dosage regimen.

Where intervention is indicated, systems of the invention can provide for rapid intervention, e.g., in 5 hours or less, such as 4 hours or less, including 3 hours or less, such as 2 hours or less, e.g., 1 hour or less. As such, embodiments of the systems can provide for intervention, e.g., in the form of excess patch removal, prior to manifestation of any adverse results. The invention can be economical, as it may be provided by a predetermined trained caregiver, such as described above, where the predetermined trained caregiver may, in some instances, require little if any compensation for providing the intervening service.

Kits

Also provided are kits that include at least one or more patches, e.g., as described above. For example, a kit may include multiple patches, where each of the patients has a uniquely identified patch tag. The kit components may be present in packaging, which packaging may be sterile, as desired.

Also present in the kit may be instructions for using the kit components. The instructions may be recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or sub-packaging) etc. In other embodiments, the instructions are present as an electronic storage data file present on a suitable computer readable storage medium, e.g., portable flash drive, DVD- or CD-ROM, etc. The instructions may take any form, including complete instructions for how to use the device or as a website address with which instructions posted on the world wide web may be accessed.

The following example(s) is/are offered by way of illustration and not by way of limitation.

EXAMPLE

I. Monitoring of Exelon Patch Dosage Regimen
A. Monitoring System

An elderly patient suffering from Alzheimer's Disease is prescribed an Exelon® rivastigmine 9.5 mg patch dosage regimen in accordance with FDA approved instructions for use, where a new 9.5 mg rivastigmine patch is applied to the patient's skin every 24 hours such only a single patch is applied to the patient at any one time. The 9.5 mg rivastigmine patches employed in the patch dosage regimen include a Bluetooth Low Energy (BLE) tag which includes a unique identifier. Compliance of the patient with the prescribed patch dosage regimen is monitored with a smart intervention system (SIS) as illustrated in FIG. 3.

Figure 3:
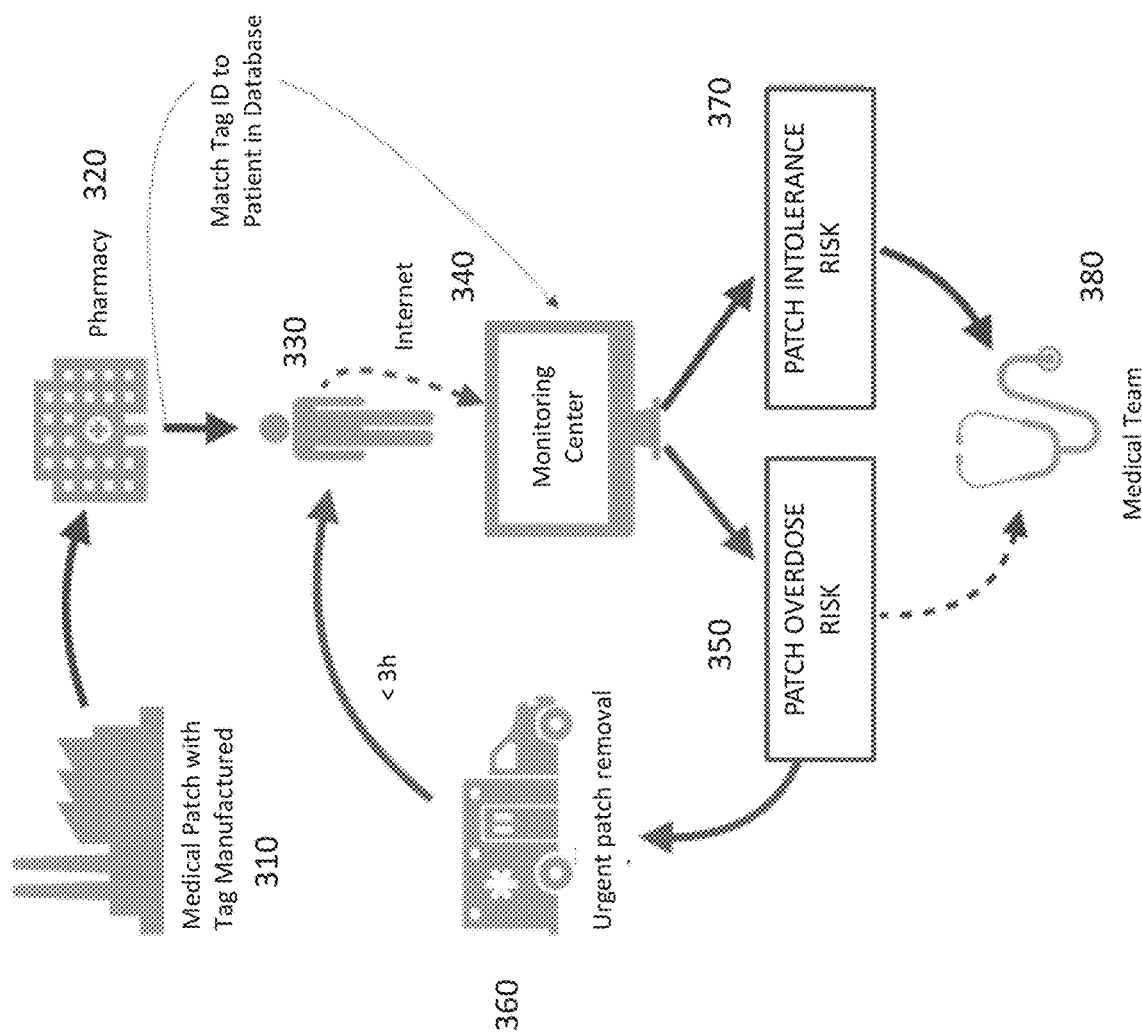
FIG. 3 illustrates a smart intervention system (SIS) for monitoring compliance of a patient with a rivastigmine patch dosage regimen in accordance with an embodiment of the invention.

As shown in FIG. 3, 9.5 mg rivastigmine patches that include a BLE patch tag, e.g., as illustrated in FIG. 1, are manufactured at factory 310. A set of manufactured patches are then forwarded to pharmacy 320, where the unique identifiers of the patch tags of each of the patches in the set are matched with provided to the patient 330. As shown, the number of patches that is applied to the patient at any given time is then forwarded to a monitoring center 340 that includes a compliance determination module. An event manager at the monitoring center receives information from the compliance determination module and, if the information indicates that the patient is deviated from the prescribed patch dosage regimen, takes one of two actions. As illustrated, if the compliance information indicates that the patient has more than one patch applied thereto, the event manager determines that there is a patch overdose risk 350. Following such determination, the event manager contacts one of a set of predetermined non-health care professional care givers, such as a spouse, son/daughter, friend, to interact with the patient and remove the extra patch. If such is not possible, the event manager then contacts emergency medical services (EMS) 360 to effect urgent patch removal. Alternatively, if the compliance information indicates that the patient has no patches applied thereto, the event manager determines that there is a patch intolerance risk 370. As indicated, the event manager may then relay the compliance information to the patient's medical team 380.

Figure 4A:
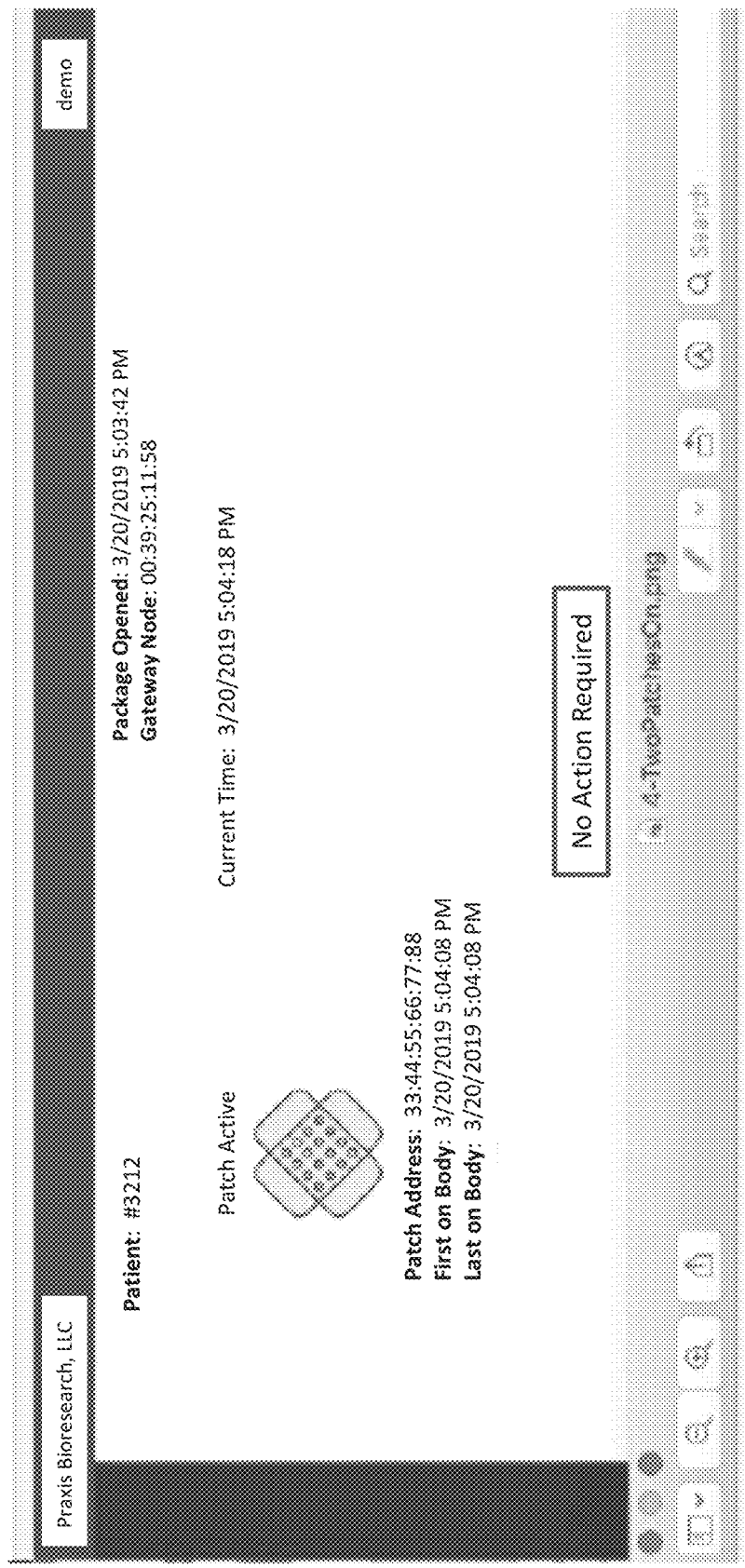
FIGS. 4A to 4B provide different views of how compliance information may be presented to an event manager in the system illustrated in FIG. 2.
Figure 4B:
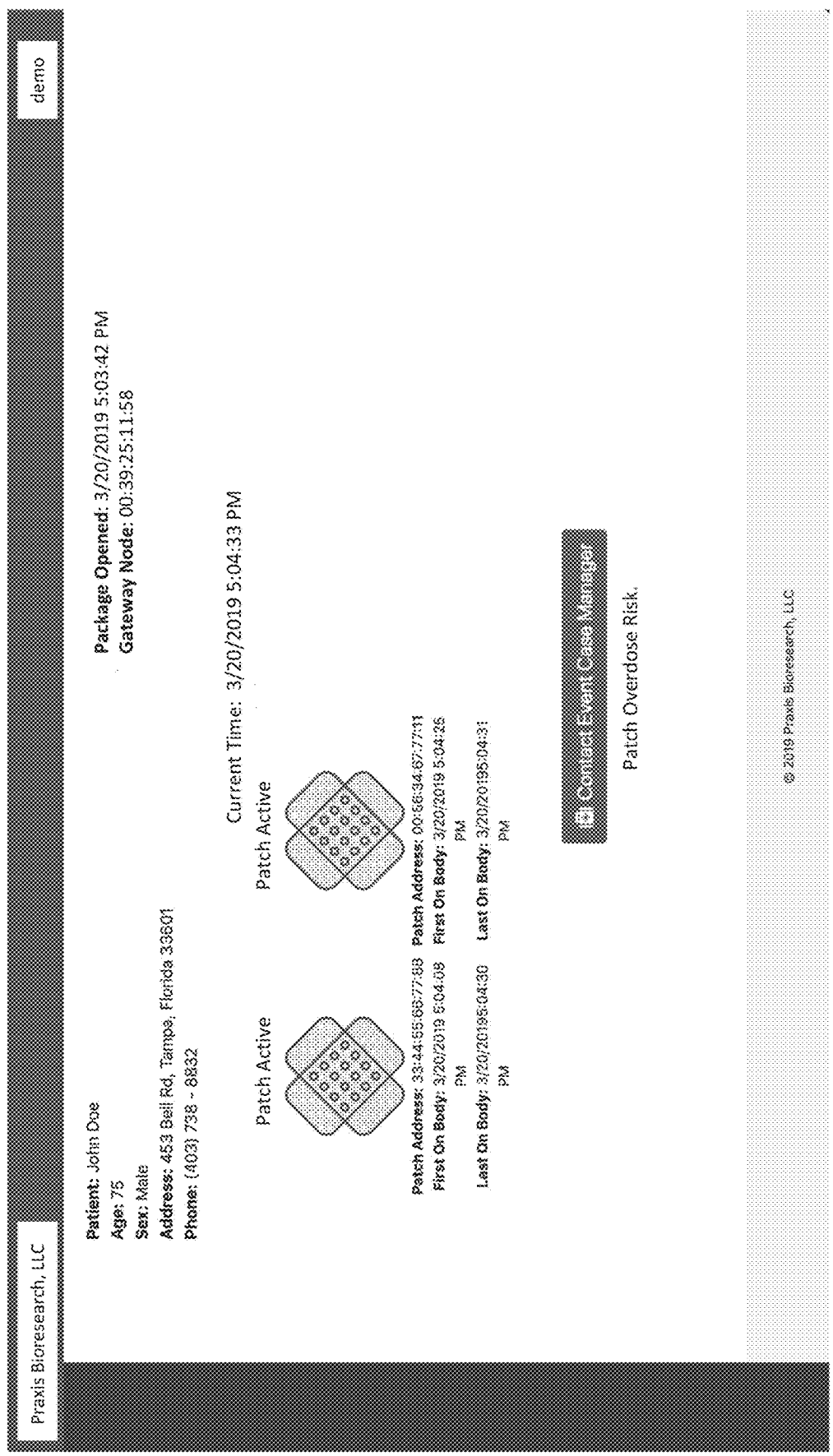

FIGS. 4A to 4B provide different views of how compliance information may be presented to an event manager in the system illustrated in FIG. 2. In FIG. 4A, compliance information indicates a single active patch is present on the body of the patient, where the provided information includes the unique identifier, as well as the time applied, and the last time detected on the body. The compliance information also indicates that no action is required. In FIG. 4B, two active patches are shown having been applied to the body at the same time, indicating a patch overdose risk.

FIG. 5 provides a flow chart 500 illustrating the process that is employed when a patch overdose risk is identified by the smart intervention system shown in FIG. 2. In the process shown in FIG. 5, following determination of a patch overdose event 510 and confirmation of patient, address and patch dosage regimen 520, an event manager assesses the compliance information and determines that intervention is necessary 530. As illustrated, the event manager then contacts a predetermined caregiver from a predetermined selection of such caregivers 540, e.g., from a database as described above. If a predetermined caregiver is available 550, the event manager instructs the caregiver to intervene 560 and remove the extra patch 570. If a predetermined caregiver is not available 580, the event manager instructs a nearest emergency response team 590 to intervene and remove the extra patch 570.

FIG. 6 provides a flow chart 600 illustrating the process that is employed when a patch intolerance risk is identified by the smart intervention system shown in FIG. 2. In the process shown in FIG. 65, following determination of a missed patch day event 610 and confirmation of patient, address and patch dosage regimen 620, an event manager assesses the compliance information and determines that intervention is necessary 630. As illustrated, the event manager confirms the event and patient ID and then notifies the patient's medical team that a patch application was missed 640.

Many other variations on the methods and systems described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

BIBLIOGRAPHY

[1] "A case of rivastigmine toxicity caused by transdermal patch.—PubMed—NCBI."
[2] H. Lovborg and A. K. J. and S. Hagg, "A Fatal Outcome After Unintentional Overdosing of Rivastigmine Patches," *Current Drug Safety*, 31 Jan. 2012.
[3] R. Khoury, J. Rajamanickam, and G. T. Grossberg, "An update on the safety of current therapies for Alzheimer's disease: focus on rivastigmine," *Ther. Adv. Drug Saf.*, vol. 9, no. 3, pp. 171-178, March 2018.
[4] G. Lefévre et al., "Pharmacokinetics and pharmacodynamics of the novel daily rivastigmine transdermal patch compared with twice-daily capsules in Alzheimer's disease patients," *Clin. Pharmacol. Ther.*, vol. 83, no. 1, pp. 106-114, January 2008.
[5] A. Kurz, M. Farlow, and G. Lefévre, "Pharmacokinetics of a novel transdermal rivastigmine patch for the treatment of Alzheimer's disease: a review," *Int. J. Clin. Pract.*, vol. 63, no. 5, pp. 799-805, 2009.
[6] "Drugs@FDA: FDA Approved Drug Products." [Online]. Available: https://www.accessdata.fda.gov/scripts/cder/daf/index.cfm?event=overview.process&ApplNo=022083.

What is claimed is:

1. A system for monitoring compliance of a patient with a patch dosage regimen and, where necessary, providing rapid, economical intervention when non-compliance is detected, the system comprising:
   a) a patch comprising an active agent and a patch tag, wherein the active agent comprises a cholinesterase inhibitor;
   b) a reader configured to detect the patch tag; and
   c) a compliance determination module comprising a computer-readable storage medium comprising instructions that, when executed by one or more processing devices, (i) determine compliance information from data received from the reader, wherein the compliance information includes data that may be employed to determine whether the patient is complying with the patch dosage regimen, and (ii) alert a predetermined trained caregiver selected from a list of two or more predetermined trained caregivers if the patient is in non-compliance with the patch dosage regimen, wherein the predetermined trained caregiver is not a healthcare professional; and further wherein: the alert comprises instructions for the predetermined trained caregiver to remove the patch; the system is configured to provide the instructions for the predetermined trained caregiver to remove the patch only within 3 hours or less of determination of non-compliance; and the system is configured to alert a health care professional in excess of 3 hours of determination of non-compliance.

2. The system according to claim 1, wherein the compliance information comprises a determination of a number of patches applied to a patient.

3. The system according to claim 2, wherein the patient is determined to be in non-compliance with the patch dosage regimen if a determination of a number of patches applied to a patient deviates from the patch dosage regimen.

4. The system according to claim 2, wherein the patch dosage regimen is a single patch at a time.

5. The system according to claim 1, wherein the compliance determination module is further configured to output the compliance information to an event manager.

6. The system according to claim 1, wherein the compliance determination module generates an alarm if the patient is determined to be in non-compliance with the patch dosage regiment.

7. The system according to claim 1, wherein the reader communicates wirelessly with the patch tag.

8. The system according to claim 1, wherein the reader is part of a device that is distinct from the device comprising the compliance determination module.

9. The system according to claim 8, wherein the reader is a component of a gateway.

10. The system according to claim 1, wherein the patch tag is configured to be detectable only when applied to a dermal surface of the patient.

11. The system according to claim 1, wherein the patch tag comprises a unique identifier.

12. The system according to claim 11, wherein the unique identifier has been linked to the patient.

13. The system according to claim 1, wherein the patch tag comprises a power source.

14. The system according to claim 1, wherein the patch tag comprises a Bluetooth Low Energy (BLE) tag.

15. The system according to claim 1, wherein the patch tag comprises a RFID tag.

16. The system according to claim 15, wherein the RFID tag is passive.

17. The system according to claim 1, wherein the patient suffers from a cognitive disorder.

18. The system according to claim 17, wherein the cognitive disorder is Alzheimer's disease or Parkinson's disease.

19. The system according to claim 1, wherein the patch tag is configured to be activated at the time of administration and the reader is configured automatically detect the patch tag.

* * * * *